United States Patent
Miller et al.

(10) Patent No.: US 10,502,729 B2
(45) Date of Patent: Dec. 10, 2019

(54) DIAGNOSTIC METHODS, THERAPEUTIC AGENTS AND USES THEREOF

(71) Applicant: Metabolon, Inc., Morrisville, NC (US)

(72) Inventors: Luke Miller, Bahama, NC (US); Klaus Peter Adam, Cary, NC (US); Michael V. Milburn, Cary, NC (US); Jeffery E. Cobb, Chapel Hill, NC (US); Anne M. Evans, Cary, NC (US); Qibo Zhang, Cary, NC (US)

(73) Assignee: Metabolon, Inc., Morrisville, NC (US)

( * ) Notice: Subject to any disclaimer, the term of this patent is extended or adjusted under 35 U.S.C. 154(b) by 0 days.

(21) Appl. No.: 15/548,854

(22) PCT Filed: Feb. 4, 2016

(86) PCT No.: PCT/US2016/016536
§ 371 (c)(1),
(2) Date: Aug. 4, 2017

(87) PCT Pub. No.: WO2016/126923
PCT Pub. Date: Aug. 11, 2016

(65) Prior Publication Data
US 2018/0031541 A1 Feb. 1, 2018

Related U.S. Application Data

(60) Provisional application No. 62/113,113, filed on Feb. 6, 2015.

(51) Int. Cl.
*C07D 307/33* (2006.01)
*G01N 33/50* (2006.01)
*C07K 16/44* (2006.01)

(52) U.S. Cl.
CPC ........... *G01N 33/50* (2013.01); *C07D 307/33* (2013.01); *C07K 16/44* (2013.01); *G01N 33/5008* (2013.01); *C07K 2317/56* (2013.01); *C07K 2319/00* (2013.01); *G01N 2800/042* (2013.01); *G01N 2800/52* (2013.01)

(58) Field of Classification Search
CPC .............................. G01N 33/50; C07D 307/33
USPC ....................................................... 549/295
See application file for complete search history.

(56) References Cited

FOREIGN PATENT DOCUMENTS

| WO | WO-2013/006278 A2 | 1/2013 |
|---|---|---|
| WO | WO-2013/039898 A1 | 3/2013 |

OTHER PUBLICATIONS

Walter Gall et al. a-Hydroxybutyrate is an Early Biomarker of Insulin Resistance and Glucose Intolerance in a Nondiabetic Population (Year: 2010).*
Jeff Cobb et al. A Novel Test for IGT Utilizing Metabolite Markers of Glucose Tolerance (Year: 2014).*
Mariya Kolesnikova et al. sterochennistry of water addition in Triterpene Synthesis: The structure of Arabidiol. (Year: 2007).*
Gall et al.; "α-Hydroxybutyrate Is an Early Biomarker of Insulin Resistance and Glucose Intolerance in a NonDiabetic Population"; PLOS ONE; 5(5):e10883 (May 28, 2010).
Cobb et al.; "A novel Test for IGT Utilizing Metabolite markers of Glucose tolerance"; Journal of Diabetes Science and Technology; 9(1):69-76 (Sep. 26, 2014).
Albrecht et al.; "Metabolite Profiling Reveals New Insights into the Regulation of Serum Urate in Humans"; Metabolomics; 10(1):141-151 (Feb. 1, 2014).
Kolesnikova et al.; "Stereochemistry of Water Addition in Triterpene Synthesis: The Structure of Arabidiol"; Organic Letters; 9(11):2183-2186 (May 1, 2007).

* cited by examiner

*Primary Examiner* — Rita J Desai
(74) *Attorney, Agent, or Firm* — McCarter & English, LLP; Xin Zhang

(57) ABSTRACT

The present invention provides a method for diagnosing a disease or disorder selected from the group consisting of insulin resistance, a metabolic disorder, diabetes and pre-diabetes in a subject. The method comprises the step of determining the level of a compound represented by structural formula (VI): or a salt thereof. Compositions and method of making thereof are also described.

(VI)

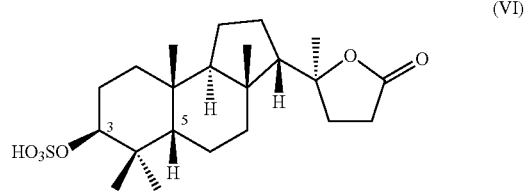

6 Claims, 1 Drawing Sheet

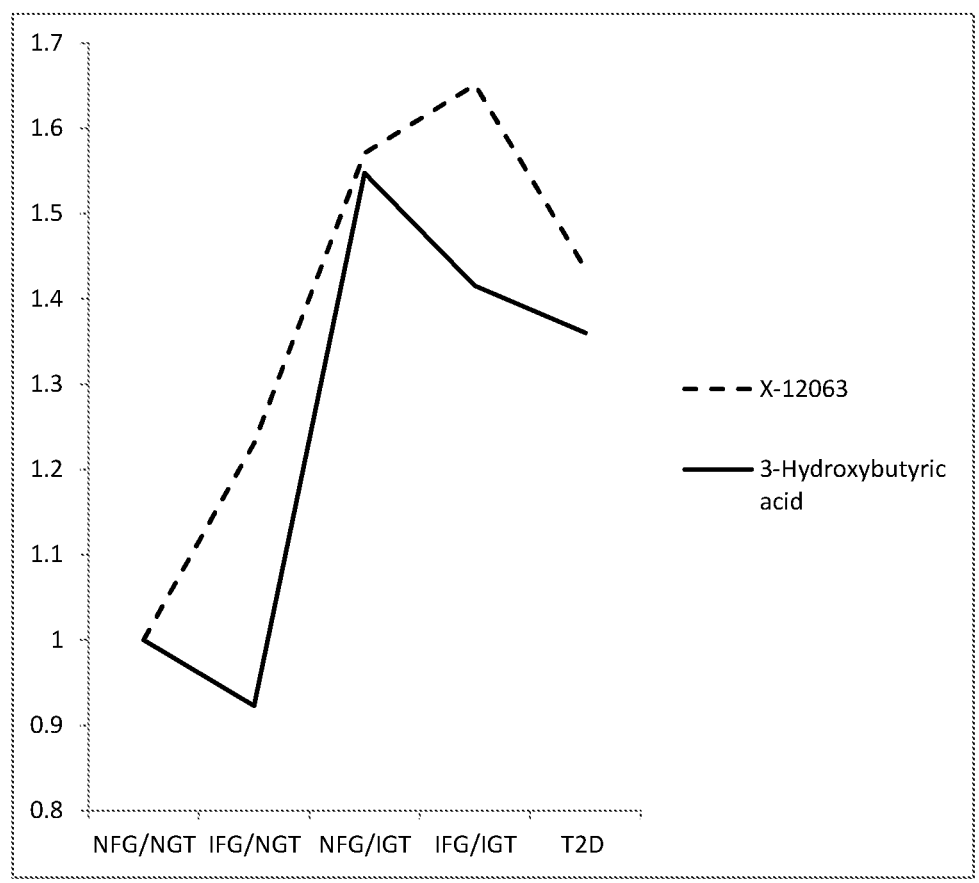

DIAGNOSTIC METHODS, THERAPEUTIC AGENTS AND USES THEREOF

REFERENCE TO RELATED APPLICATIONS

This application is a 35 U.S.C. § 371 national stage filing of International Application No. PCT/US2016/016536, filed on Feb. 4, 2016, which claims the benefit of the filing date, under 35 U.S.C. § 119(e), of U.S. Provisional Application No. 62/113,113, filed on Feb. 6, 2015. The entire content of each of these applications is incorporated herein by reference.

BACKGROUND OF THE INVENTION

Diabetes is classified as either type 1 (early onset) or type 2 (adult onset), with type 2 comprising 90-95% of the cases of diabetes. Diabetes is the final stage in a disease process that begins to affect individuals long before the diagnosis of diabetes is made. Type 2 diabetes develops over 10 to 20 years and results from an impaired ability to utilize glucose (glucose utilization) due to impaired sensitivity to insulin (insulin resistance).

In pre-diabetes, insulin becomes less effective at helping tissues metabolize glucose. Pre-diabetics may be detectable as early as 20 years before diabetic symptoms become evident. Studies have shown that although patients show very few symptoms, long-term physiological damage is already occurring at this stage. Up to 60% of these individuals will progress to type 2 diabetes within 10 years.

The American Diabetes Association (ADA) has recommended routine screening to detect patients with pre-diabetes. Current screening methods for pre-diabetes include fasting plasma glucose (FPG), the oral glucose tolerance test (OGTT), hemoglobin A1c, fasting insulin, and the hyperinsulinemic euglycemic clamp (HI clamp). The first three methods are used clinically whereas the latter two tests are used extensively in research but rarely in the clinic. In addition, mathematical means (e.g., HOMA, QUICKI) that consider the fasting glucose and insulin levels together have been proposed. However, normal plasma insulin concentrations vary considerably between individuals as well as within an individual throughout the day. Further, these methods suffer from variability and methodological differences between laboratories and do not correlate rigorously with HI clamp studies.

Worldwide, an estimated 194 million adults have type 2 diabetes and this number is expected to increase to 333 million by 2025, largely due to the epidemic of obesity in westernized societies. In the United States, it is estimated that over 54 million adults are pre-diabetic, depending on the level of insulin resistance. There are approximately 1.5 million new cases of type 2 diabetes a year in the United States. The annual US healthcare cost for diabetes is estimated at $174 billion. This figure has risen more than 32% since 2002. In industrialized countries such as the U.S., about 25% of medical expenditures treat glycemic control, 50% is associated with general medical care associated with diabetes, and the remaining 25% of the costs go to treat long-term complications, primarily cardiovascular disease. Considering the distribution of the healthcare costs and the fact that insulin resistance is a direct causal factor in cardiovascular disease and diabetes progression, it is no surprise that cardiovascular disease accounts for 70-80% of the mortality observed for diabetic patients. Detecting and preventing type 2 diabetes has become a major health care priority.

Diabetes may also lead to the development of other diseases or conditions, or is a risk factor in the development of conditions such as Metabolic Syndrome and cardiovascular diseases. Metabolic Syndrome is the clustering of a set of risk factors in an individual. According to the American Heart Association these risk factors include: abdominal obesity, decreased ability to properly process glucose (insulin resistance or glucose intolerance), dyslipidemia (high triglycerides, high LDL, low HDL cholesterol), hypertension, prothrombotic state (high fibrinogen or plasminogen activator inhibitor-1 in the blood) and proinflammatory state (elevated C-reactive protein in the blood). Metabolic Syndrome is also known as syndrome X, insulin resistance syndrome, obesity syndrome, dysmetabolic syndrome and Reaven's syndrome. Patients diagnosed with Metabolic Syndrome are at an increased risk of developing diabetes, cardiac and vascular disease. It is estimated that, in the United States, 20% of the adults (>50 million people) have metabolic syndrome. While it can affect anyone at any age, the incidence increases with increasing age and in individuals who are inactive, and significantly overweight, especially with excess abdominal fat.

Type 2 diabetes is the most common form of diabetes in the United States. According to the American Diabetes Foundation over 90% of the US diabetics suffer from type 2 diabetes. Individuals with type 2 diabetes have a combination of increased insulin resistance and decreased insulin secretion that combine to cause hyperglycemia. Most persons with type 2 diabetes have Metabolic Syndrome.

The diagnosis for Metabolic Syndrome is based upon the clustering of three or more of the risk factors in an individual. There are no well-accepted criteria for diagnosing the metabolic syndrome. The criteria proposed by the National Cholesterol Education Program (NCEP) Adult Treatment Panel III (ATP III), with minor modifications, are currently recommended and widely used.

The American Heart Association and the National Heart, Lung, and Blood Institute recommend that the metabolic syndrome be identified as the presence of three or more of these components: increased waist circumference (Men—equal to or greater than 40 inches (102 cm), Women—equal to or greater than 35 inches (88 cm); elevated triglycerides (equal to or greater than 150 mg/dL); reduced HDL ("good") cholesterol (Men—less than 40 mg/dL, Women—less than 50 mg/dL); elevated blood pressure (equal to or greater than 130/85 mm Hg); elevated fasting glucose (equal to or greater than 100 mg/dL).

Type 2 diabetes develops slowly and often people first learn they have type 2 diabetes through blood tests done for another condition or as part of a routine exam. In some cases, type 2 diabetes may not be detected before damage to eyes, kidneys or other organs has occurred. A need exists for an objective, biochemical evaluation (e.g. lab test) that can be administered by a primary care provider to identify individuals that are at risk of developing Metabolic Syndrome or type 2 diabetes.

Newer, more innovative molecular diagnostics that reflect the mechanisms of the patho-physiological progression to pre-diabetes and diabetes are needed because the prevalence of pre-diabetes and diabetes is increasing in global epidemic proportions. Mirroring the obesity epidemic, pre-diabetes and diabetes are largely preventable but are frequently undiagnosed or diagnosed too late due to the asymptomatic nature of the progression to clinical disease.

Therefore there is an unmet need for diagnostic biomarkers and tests that can identify pre-diabetics at risk of developing type 2 diabetes and to determine the risk of disease progression in subjects with insulin resistance. Insulin resistance biomarkers and diagnostic tests can better identify and determine the risk of diabetes development in a pre-diabetic subject, can monitor disease development and progression and/or regression, can allow new therapeutic treatments to be developed and can be used to test therapeutic agents for efficacy on reversing pre-diabetes and/or preventing diabetes. Further, a need exists for diagnostic biomarkers to more effectively assess the efficacy and safety of pre-diabetic and diabetic therapeutic candidates.

SUMMARY OF THE INVENTION

The present invention provides novel compounds (such as compounds represented by formula (I), (II), (III), (IV), (V), (VI), (VII) or compound A or a salt or a pharmaceutically acceptable salt thereof) and pharmaceutical compositions comprising thereof. Further, the present invention provides diagnostic methods, wherein the compounds described herein (such as compounds of formulas (I), (II), (III), (IV), (V), (VI), (VII) or compound A or a salt or a pharmaceutically acceptable salt thereof) serve as prognostics or diagnostic indicators of pre-diabetes, diabetes, insulin resistance, or metabolic disorders associated with changes in insulin activity.

In one embodiment, the present invention provides a method for diagnosing a disease or disorder selected from the group consisting of insulin resistance, a metabolic disorder, diabetes and pre-diabetes in a subject comprising: determining the level of a compound represented by formula (IV):

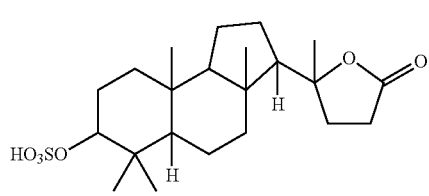

(IV)

or a salt thereof, in a biological sample from the subject, wherein the level of the compound is determined by chromatography, mass spectrometry, enzyme-linked immunosorbent assay (ELISA), antibody linkage, or other immunochemical methods, and wherein an elevated level of the compound in the biological sample as compared to the level of the compound in a normal control sample is indicative of the disease or disorder in the subject.

In one embodiment, the present invention provides a method for diagnosing a disease or disorder selected from the group consisting of insulin resistance, a metabolic disorder, diabetes and pre-diabetes in a subject comprising: determining the level of a compound represented by formula (VI):

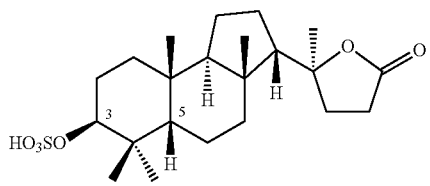

or a salt thereof, in a biological sample from the subject, wherein the level of the compound is determined by chromatography, mass spectrometry, enzyme-linked immunosorbent assay (ELISA), antibody linkage, or other immunochemical methods, and wherein an elevated level of the compound in the biological sample as compared to the level of the compound in a normal control sample is indicative of the disease or disorder in the subject.

In another embodiment, the present invention provides a method for monitoring the progression or regression of a disease or disorder selected from the group consisting of insulin resistance, a metabolic disorder, diabetes and pre-diabetes in a subject comprising:

(1) determining the level of a compound represented by formula (IV):

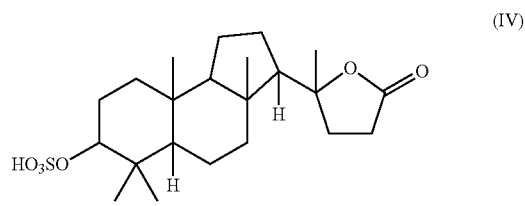

(IV)

or a salt thereof, in a biological sample from the subject, (2) determining the level of the compound in a second biological sample obtained from the subject at a second time, wherein the second time is later than the first time;

wherein a change in the level of the compound is indicative of progression or regression of the disease in the subject and wherein the level of the compound is determined by chromatography, mass spectrometry, enzyme-linked immunosorbent assay (ELISA), antibody linkage, or other immunochemical methods.

In another embodiment, the present invention provides a method for monitoring the progression or regression of a disease or disorder selected from the group consisting of insulin resistance, a metabolic disorder, diabetes and pre-diabetes in a subject comprising:

(1) determining the level of a compound represented by formula (VI):

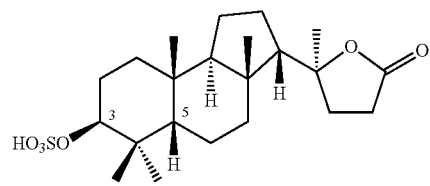

or a salt thereof, in a biological sample from the subject, (2) determining the level of the compound in a second biological sample obtained from the subject at a second time, wherein the second time is later than the first time;

wherein a change in the level of the compound is indicative of progression or regression of the disease in the subject and wherein the level of the compound is determined by chromatography, mass spectrometry, enzyme-linked immunosorbent assay (ELISA), antibody linkage, or other immunochemical methods.

In yet another embodiment, the present invention provides a method for monitoring the efficacy of a therapy for treating insulin resistance, a metabolic disorder, diabetes or pre-diabetes in a subject, the method comprising the steps of:

(1) determining the level of a compound represented by formula (IV):

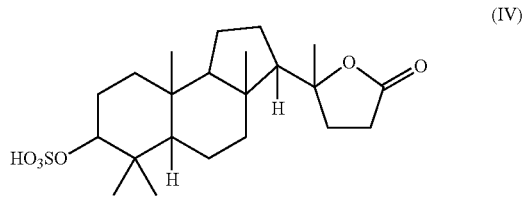

(IV)

or a salt thereof, in a biological sample from the subject;

(2) treating the subject with the therapy for insulin resistance, a metabolic disorder, diabetes or pre-diabetes;

(3) analyzing a second biological sample from the subject to determine the level of the compound, wherein the second sample is obtained from the subject at a time point after the treatment; and (4) comparing the level of the compound in the first sample to the level of the compound in the second sample to assess the efficacy of the treatment for treating insulin resistance, a metabolic disorder, diabetes or pre-diabetes, wherein the level of the compound is determined by chromatography, mass spectrometry, enzyme-linked immunosorbent assay (ELISA), antibody linkage, or other immunochemical methods.

In yet another embodiment, the present invention provides a method for monitoring the efficacy of a therapy for treating insulin resistance, a metabolic disorder, diabetes or pre-diabetes in a subject, the method comprising the steps of:

(1) determining the level of a compound represented by formula (VI):

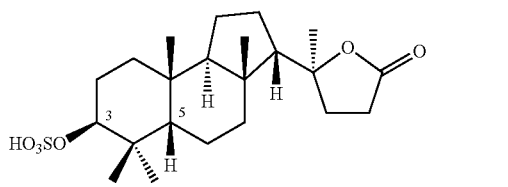

or a salt thereof, in a biological sample from the subject;

(2) treating the subject with the therapy for insulin resistance, a metabolic disorder, diabetes or pre-diabetes;

(3) analyzing a second biological sample from the subject to determine the level of the compound, wherein the second sample is obtained from the subject at a time point after the treatment; and (4) comparing the level of the compound in the first sample to the level of the compound in the second sample to assess the efficacy of the treatment for treating insulin resistance, a metabolic disorder, diabetes or pre-diabetes, wherein the level of the compound is determined by chromatography, mass spectrometry, enzyme-linked immunosorbent assay (ELISA), antibody linkage, or other immunochemical methods.

In another embodiment, the present invention provides a method of treating a disease or disorder selected from the group consisting of insulin resistance, a metabolic disorder, diabetes and pre-diabetes in a subject comprising administrating an effective therapy suitable for treating the disease or disorder to the subject, wherein the subject has an elevated level of a compound represented by the following formula:

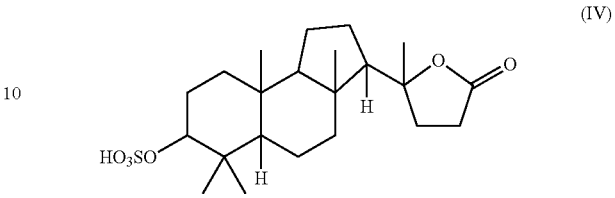

(IV)

or a salt thereof, as compared to a normal control subject.

In yet another embodiment, the present invention provides a method of treating a disease or disorder selected from the group consisting of insulin resistance, a metabolic disorder, diabetes and pre-diabetes in a subject comprising administrating an effective therapy suitable for treating the disease or disorder to the subject, wherein the subject has an elevated level of a compound represented by the following formula:

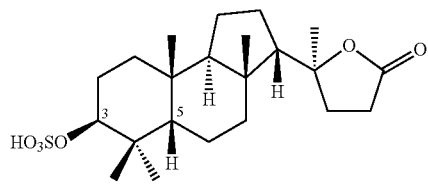

or a salt thereof, as compared to a normal control subject.

The present invention also provides a method of treating a disease or disorder selected from the group consisting of insulin resistance, a metabolic disorder, diabetes and pre-diabetes in a subject comprising:

(1) determining the level of a compound represented by the following formula:

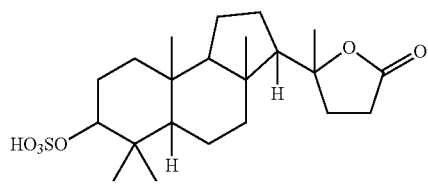

or a salt thereof, in a biological sample from the subject by chromatography, mass spectrometry, enzyme-linked immunosorbent assay (ELISA), or other immunochemical methods; and 2) administrating an effective therapy suitable for treating the disease or disorder to the subject when the subject has an elevated level of the compound as compared to the level of the compound in a normal control sample.

The present invention also provides a method of treating a disease or disorder selected from the group consisting of insulin resistance, a metabolic disorder, diabetes and pre-diabetes in a subject comprising:

(1) determining the level of a compound represented by the following formula:

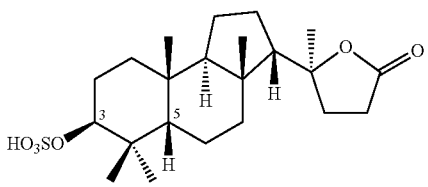

or a salt thereof, in a biological sample from the subject by chromatography, mass spectrometry, enzyme-linked immunosorbent assay (ELISA), or other immunochemical methods; and 2) administering an effective therapy suitable for treating the disease or disorder to the subject when the subject has an elevated level of the compound as compared to the level of the compound in a normal control sample.

In one embodiment, the present invention is directed to a compound represented by the following formula:

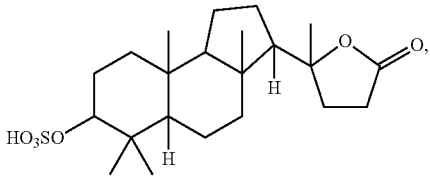

or a salt thereof, wherein the compound is substantially free of impurities.

In yet another embodiment, the present invention is directed to a compound represented by

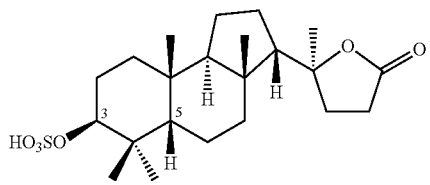

or a salt thereof, wherein the compound is substantially free of impurities.

In yet another embodiment, the present invention provides a compound represented by the following formula:

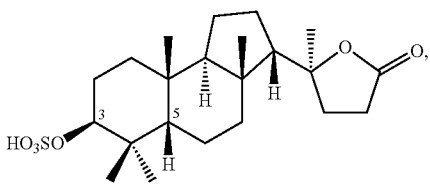

or a salt thereof.

The present invention also provides a kit comprising at least one compound of the present invention and instructions for diagnosing and/or monitoring a disease or disorder selected from the group consisting of insulin resistance, a metabolic disorder, diabetes and pre-diabetes in a subject based on the level of the compound detected in a biological sample from the subject.

Also provided is methods of preparing the compounds of the present invention.

In one embodiment, the present invention provides compounds according to formula (I):

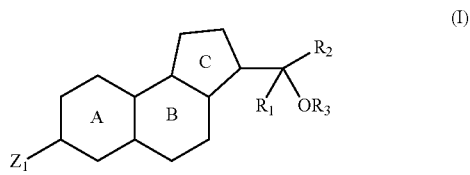

or a salt (e.g., a pharmaceutically acceptable salt) thereof, wherein:

rings A, B and C are optionally substituted with one or more substituents selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl;

Z$_1$ is —OH, —OR$^a$, —OSO$_3$H, —OPO(OH)$_2$, —OC(=O)R$^b$, —OC(=O)NR$^c$R$^d$ or =O;

R$_1$ is a (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

R$_2$ is H, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

R$_3$ is H, —C(=O)R$^b$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

or OR$_3$ together with R$_2$ forms a 3 to 9 membered ring optionally substituted with =O, (C$_1$-C$_6$)alkyl, —OH or —OR$^a$;

R$^a$ is (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl ($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R^b$ is H or a ($C_1$-$C_6$)alkyl;

$R^c$ and $R^d$ are each independently H or a ($C_1$-$C_6$)alkyl; and $R^e$, $R^f$, $R^g$ and $R^h$ are each independently H or a ($C_1$-$C_6$)alkyl;

wherein each of ($C_1$-$C_6$)alkyl, ($C_2$-$C_6$) alkenyl, ($C_2$-$C_6$) alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, halo($C_1$-$C_6$)alkyl and hydroxyl($C_1$-$C_6$)alkyl.

Another embodiment of the invention is a pharmaceutical composition comprising a pharmaceutically acceptable carrier or diluent and a compound represented by Structural Formula (I) or a pharmaceutically acceptable salt thereof.

Another embodiment of the invention is a method of diagnosing insulin resistance, a metabolic disorder, diabetes or pre-diabetes in a subject. The method comprises determining the level of a compound of formula (I), (II) or (III) in a biological sample from the subject; and comparing the level of the compound in the biological sample with the level of the compound in a normal control sample, wherein an altered level of the compound in the biological sample is indicative of the disease or disorder in the subject.

Another embodiment of the invention is a method for monitoring the progression or regression of a disease or disorder selected from insulin resistance, a metabolic disorder, diabetes and pre-diabetes in a subject. The method comprises determining the level of a compound of formula (I), (II) or (III) in a first biological sample obtained at a first time from the subject; determining the level of the compound in a second biological sample obtained from the subject at a second time, wherein the second time is later than the first time; and comparing the level of the compound in the second biological sample with the level of the compound in the first biological sample, wherein a change in the level of the compound is indicative of progression or regression of the disease or disorder in the subject.

Another embodiment of the invention is a method of monitoring the efficacy of insulin resistance treatment, a metabolic disorder treatment, diabetes treatment or pre-diabetes treatment in a subject, the method comprising determining the level of a compound of formula (I), (II) or (III) in a biological sample from the subject; treating the subject for insulin resistance, a metabolic disorder, diabetes or pre-diabetes; analyzing a second biological sample from the subject to determine the level of the compound of formula (I), (II) or (III), wherein the second sample obtained from the subject at a second time point after treatment; and comparing the level of the compound of formula (I), (II) or (III) in the first sample to the level of the compound of formula (I), (II) or (II) in the second sample to assess the efficacy of the treatment for treating insulin resistance, a metabolic disorder, diabetes or pre-diabetes.

BRIEF DESCRIPTION OF THE DRAWINGS

FIG. 1 provides an example of plasma levels of X12063 and 3-hydroxybutryic acid measured in samples from Normal (NFG/NGT) subjects and dysglycemic subjects (IFG/NGT, NFG/IGT, IFG/IGT and T2D). NFG/NGT indicates Normal Fasting Glucose and Normal Glucose Tolerance; IFG/NGT indicates Impaired Fasting Glucose and Normal Glucose Tolerance; NFG/IGT indicates Normal Fasting Glucose and Impaired Glucose Tolerance; IFG/IGT indicates Impaired Fasting Glucose and Impaired Glucose Tolerance; and T2D indicates Type 2 Diabetes.

DETAILED DESCRIPTION OF THE INVENTION

Definitions

Unless otherwise specified, the below terms used herein are defined as follows:

In the groups, radicals, or moieties defined below, the number of carbon atoms is often specified preceding the group. For example, ($C_1$-$C_6$)alkyl means an alkyl group or radical having 1 to 6 carbon atoms. In general, for groups comprising two or more subgroups, the last named subgroup is the radical attachment point. For example, the substituent "aryl($C_1$-$C_3$)alkyl" means an aryl group which is bound to a ($C_1$-$C_3$)alkyl group, the latter of which is bound to the core or to the group to which the substituent is attached.

"Alkyl" means a saturated aliphatic branched or straight-chain monovalent hydrocarbon radical having the specified number of carbon atoms. For example, "($C_1$-$C_6$)alkyl" means a radical having from 1-6 carbon atoms in a linear or branched arrangement. "($C_1$-$C_6$)alkyl" includes methyl, ethyl, propyl, butyl, pentyl, and hexyl.

"Alkenyl" means branched or straight-chain monovalent hydrocarbon radical containing at least one double bond and having specified number of carbon atoms. Alkenyl may be mono or polyunsaturated, and may exist in the E or Z configuration. For example, "($C_2$-$C_6$)alkenyl" means a radical having from 2-6 carbon atoms in a linear or branched arrangement.

"Alkynyl" means branched or straight-chain monovalent hydrocarbon radical containing at least one triple bond and having specified number of carbon atoms. For example, "($C_2$-$C_6$)alkynyl" means a radical having from 2-6 carbon atoms in a linear or branched arrangement.

"Cycloalkyl" means a saturated aliphatic cyclic hydrocarbon radical having the specified number of carbon atoms. It can be monocyclic, bicyclic, polycyclic (e.g., tricyclic), fused, bridged, or spiro. For example, monocyclic ($C_3$-$C_8$) cycloalkyl means a radical having from 3-8 carbon atoms arranged in a monocyclic ring. Monocyclic ($C_3$-$C_8$)cycloalkyl includes but is not limited to cyclopropyl, cyclobutyl, cyclopentyl, cyclohexyl, cycloheptyl and cyclooctane.

Monocyclic ring systems have a single ring structure. They include saturated or unsaturated aliphatic cyclic hydrocarbon rings or aromatic hydrocarbon ring having the specified number of carbon atoms. The monocyclic ring system can optionally contain 1 to 3 heteroatoms in the ring structure and each heteroatom is independently selected from the group consisting O, N and S. When the heteroatom is a ring nitrogen atom connected to other ring atoms only by single bonds, it can be substituted. Exemplary substituents, unless otherwise indicated, include —H, alkyl, cycloalkyl, cycloalkylalkyl, aryl, arylalkyl, heteroaryl, heteroarylalkyl (preferably, —H, ($C_1$-$C_6$)alkyl, halo($C_1$-$C_6$) alkyl or ($C_1$-$C_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—)

Examples of monocyclic ring system include, but are not limited to, monocyclic cycloalkyls (e.g., cyclopropyl, cyclobutyl, cyclopentyl, cyclohexyl, cycloheptyl, cyclooctane), partially unsaturated cycloalkyls; monocyclic heterocycloalkyls (e.g., azetidine, pyrrolidine, piperidine, piperazine, hexahydropyrimidine, tetrahydrofuran, tetrahydropyran, oxepane, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine, tetrahydro-2H-1,2-thiazine 1,1-dioxide, and isothiazolidine 1,1-dioxide, tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one); monocyclic aryls (e.g., phenyl) and monocyclic heteroaryls (see descriptions below).

Bicyclic ring systems have two rings that have at least one ring atom in common. Bicyclic ring systems include fused, bridged and spiro ring systems. The two rings can both be aliphatic (e.g., cycloalkyl or cycloheteroalkyl), both be aromatic (e.g., aryl or heteroaryl), or a combination thereof. The bicyclic ring systems can optionally contain 1 to 3 heteroatoms in the ring structure and each heteroatom is independently selected from the group consisting O, N and S. When the heteroatom is a ring nitrogen atom connected to other ring atoms only by single bonds, it can be substituted. Exemplary substituents, unless otherwise indicated, include H, alkyl, cycloalkyl, cycloalkylalkyl, aryl, arylalkyl, heteroaryl, heteroarylalkyl (preferably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

A fused bicyclic ring system has two rings which have two adjacent ring atoms in common. The two rings can both be aliphatic (e.g., cycloalkyl or cycloheteroalkyl), both be aromatic (e.g., aryl or heteroaryl), or a combination thereof. For example, the first ring can be monocyclic cycloalkyl or monocyclic cycloheteroalkyl, and the second ring can a cycloalkyl, partially unsaturated carbocycle, aryl, heteroaryl or a monocyclic cycloheteroalkyl. For example, the second ring can be a $(C_3-C_6)$cycloalkyl, such as cyclopropyl, cyclobutyl, cyclopentyl and cyclohexyl. Alternatively, the second ring can be an aryl ring, e.g., phenyl.

Examples of fused bicyclic ring systems include, but not limited to, 6,7,8,9-tetrahydro-5H-benzo[7]annulene, 2,3-dihydro-1H-indene, octahydro-1H-indene, tetrahydronaphthalene, decahydronaphthalene, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, 5,6,7,8-tetrahydroquinoline and 5,6,7,8-tetrahydroisoquinoline and 2,3,4,5-tetrahydrobenzo[b]oxepine.

A spiro bicyclic ring system has two rings which have only one ring atom in common. The two rings can both be aliphatic (e.g., cycloalkyl or cycloheteroalkyl). For example, the first ring can be a monocyclic cycloalkyl or a monocyclic cycloheteroalkyl and the second ring can be a cycloalkyl, partially unsaturated carbocycle, or a monocyclic cycloheteroalkyl. Examples of spiral bicyclic ring system include, but are not limited to, spiro[2.2]pentane, spiro[2.3]hexane, spiro[3.3]heptane, spiro[2.4]heptane, spiro[3.4]octane, spiro[2.5]octane, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic ring system has two rings which have three or more adjacent ring atoms in common. For example, the first ring can be a monocyclic cycloalkyl or a monocyclic cycloheteroalkyl and the other ring is a cycloalkyl, partially unsaturated carbocycle, or a monocyclic cycloheteroalkyl. Examples of bridged bicyclic ring system include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane bicyclo[3.3.3]undecane, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane and 2-oxabicyclo[2.2.2]octane.

Polycyclic ring systems have more than two rings (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common. Examples of polycyclic ring system include, but not limited to, tricyclo[3.3.1.0$^{3,7}$]nonane (noradamantane) and tricyclo[3.3.1.1$^{3,7}$]decane (adamantane) and 2,3-dihydro-1H-phenalene "Heterocycle" means a saturated, unsaturated, or aromatic mono- or polycyclic-ring systems containing one or more heteroatoms independently selected from N, O or S. When the heteroatom is N, unless otherwise indicated, it can be substituted. Exemplary substituents include H, alkyl, cycloalkyl, cycloalkylalkyl, aryl, arylalkyl, heteroaryl, heteroarylalkyl (preferably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, unless otherwise indicated, it can be optionally mono- or di-oxygenated (i.e. —S(O)— or —S(O)$_2$—). A heterocycle can be a heteroaryl ring or heterocycloalkyl ring.

"Cycloheteroalkyl" or "heterocycloalkyl" means a saturated or partially saturated 4-12 membered ring radical having specified number of ring carbon atoms. The cycloheteroalkyl or heterocycloalkyl contains 1 to 4 ring heteroatoms, which may be the same or different, selected from N, O or S. The cycloheteroalkyl or heterocycloalkyl ring optionally contains one or more double bonds. It can be monocyclic, bicyclic, tricyclic, fused, bridged, or spiro. For example, $(C_3-C_9)$heterocycloalkyl means a ring radical containing 3-9 ring carbon atoms. The term "cycloheteroalkyl" or "heterocycloalkyl" is intended to include all the possible isomeric forms. When the heteroatom is a ring nitrogen atom connected to other ring atoms only by single bonds, it can be substituted. Exemplary substituents, unless otherwise indicated, include H, alkyl, cycloalkyl, cycloalkylalkyl, aryl, arylalkyl, heteroaryl, heteroarylalkyl (preferably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

Haloalkyl and halocycloalkyl include mono, poly, and perhaloalkyl groups where the halogens are independently selected from fluorine, chlorine, and bromine.

"Heteroaryl", "heteroaryl group", "heteroaryl ring", "heteroaromatic", "heteroaromatic group" and "heteroaromatic ring" are used interchangeably herein. "Heteroaryl" means a monovalent heteroaromatic monocyclic or polycyclic ring radical. Monocyclic heteroaryl rings are 5- and 6-membered aromatic heterocyclic rings containing 1 to 4 heteroatoms independently selected from N, O, and S, and include, but are not limited to furan, thiophene, pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole. Bicyclic heteroaryl rings are bicyclo[4.4.0] and bicyclo[4,3.0] fused ring systems containing 1 to 4 heteroatoms independently selected from N, O, and S, and include indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, and pteridine. "Alkoxy" means an alkyl radical attached through an oxygen linking atom. "($C_1$-$C_4$)-alkoxy" includes methoxy, ethoxy, propoxy, and butoxy.

"Aromatic", "aromatic group", "aromatic ring", "aryl", "aryl group" and "aryl ring" are used interchangeable herein.

"Aryl" means an aromatic monocyclic, or polycyclic hydrocarbon ring system. Aryl systems include, but limited to, phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Halogen" used herein refers to fluorine, chlorine, bromine, or iodine.

"Carbocycle" means 3-14 membered saturated or unsaturated aliphatic cyclic hydrocarbon ring.

"Cycloalkene" means an unsaturated and non-aromatic aliphatic cyclic hydrocarbon radical having the specified number of carbon atoms. It can be monocyclic, bicyclic, tricyclic, fused, bridged, or spiro. Thus, ($C_3$-$C_8$)cycloalkene means a radical having from 3-8 carbon atoms arranged in a ring. ($C_3$-$C_8$)cycloalkene includes cyclobutene, cyclopentene, cyclohexene, cycloheptene and cyclooctene.

The compounds of the invention may be present in the form of salts. Any suitable organic or inorganic salts are included in the present invention. In certain embodiments, the salts of the compounds of the invention refer to non-toxic "pharmaceutically acceptable salts." The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Pharmaceutically acceptable salt forms include pharmaceutically acceptable acidic/anionic or basic/cationic salts. Examples of pharmaceutically acceptable salts include, but are not limited to, mineral or organic acid salts of basic residues such as amines; alkali or organic salts of acidic residues such as carboxylic acids; and the like.

For example, such salts include, the acetate, ascorbate, benzenesulfonate, benzoate, bezylate, bicarbonate, bitartrate, bromide, calcium edetate, camsylate, carbonate, chloride, citrate, dihydrochloride, edetate, edisylate, ethane disulfonate, estolate, esylate, fumarate, glyceptate, gluconate, glutamate, glycolate, glycollylarsanilate, hexylresorcinate, hydrabamine, hydrobromide, hydrochloride, hydroxymaleate, hydroxynaphthoate, iodide, isethionate, lactate, lactobionate, malate, maleate, mandelate, methanesulfonate, mesylate, methylbromide, methylnitrate, methylsulfate, mucate, napsylate, nitrate, oxalate, pamoate, pantothenate, phenylacetate, phosphate/diphospate, polygalacturonate, propionate, salicylate, stearate, subacetate, succinate, sulfamide, sulfate, tannate, tartrate, teoclate, tosylate, triethiodide, ammonium, benzathine, chloroprocaine, colline, diethanolamine, ethylenediamine, meglumine and procaine salts. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which, for example, are useful for purifying or isolating the compounds of the present invention (e.g. trifluoroacetate salts) also comprise a part of the invention.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 95%, 99% or 99.9% by weight pure relative to the other stereoisomers. When a single enantiomer is named or depicted by structure, the depicted or named enantiomer is at least 60%, 70%, 80%, 90%, 95%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

When compounds having one or more stereocenters are depicted with particular stereochemistry for at least one stereocenter, the present invention also includes compounds that have the opposite stereochemistry at the corresponding stereocenter(s) and compounds that have no specific stereochemistry at the corresponding stereocenter(s).

As used herein, the term "therapy suitable for treating the disease or disorder" means a treatment regimen that is effective in treating the disease or disorder. A suitable therapy may involve the use of a therapeutic agent. Exemplary therapeutic agents for treating insulin resistance, a metabolic disorder, diabetes and pre-diabetes include, but are not limited to, antidiabetic and antiobesity drugs including, but not limited to, metformin, pioglitazone, rosiglitazone, acarbose, tetrahydrolipstatin, phentermine/topiramate (i.e., combination of phentermine and topiramate), bupropion/naltrexone (i.e., combination of bupropion and naltrexone), lorcaserin, liraglutide, and canagliflozin. Alternatively, a suitable therapy can involve a lifestyle modification described herein.

"Treating" a condition or disease refers to curing as well as ameliorating at least one symptom of the condition or disease.

As used herein, the term "subject" means any animal, but is preferably a mammal, such as, for example, a human, monkey, non-human primate, rat, mouse, cow, dog, cat, pig, horse, or rabbit.

As used herein, "effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day or from about 0.1 mg/kg/day to about 100 mg/kg/day.

"Metabolic disorder," as used herein, refers to disorders or diseases that result in perturbation of the normal physiological state of homeostasis due to an alteration in metabolism (anabolism and/or catabolism). An alteration in metabolism can result from an inability to break down (catabolize) a substance that should be broken down (e.g. phenylalanine) and as a result the substance and/or an intermediate substance builds up to toxic levels, or from an inability to produce (anabolize) some essential substance (e.g. insulin).

"Diabetes," as used herein, refers to a group of metabolic diseases characterized by high blood sugar (glucose) levels which result from defects in insulin secretion or action, or both.

"Type 2 diabetes," as used herein refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin.

Type 2 diabetes is also known as insulin-resistant diabetes, non-insulin dependent diabetes and adult-onset diabetes.

"Pre-diabetes," as used herein refers to one or more early diabetic conditions. Examples of pre-diabetic conditions include, but are not limited to, impaired glucose utilization, abnormal or impaired fasting glucose levels, impaired glucose tolerance, impaired insulin sensitivity and insulin resistance. Prediabetes can also be characterized by higher than normal hemoglobin A1c level (e.g., between 5.7% and 6.4% in hemoglobin A1c test). Prediabetes can be diagnosed by various blood tests, such as hemoglobin A1c test, fasting plasma glucose (FPG) test and oral glucose tolerance test (OGTT).

"Insulin resistance," as used herein, refers to the condition when cells become resistant to the effects of insulin—a hormone that regulates the uptake of glucose into cells—or when the amount of insulin produced is insufficient to maintain a normal glucose level. Cells are diminished in the ability to respond to the action of insulin in promoting the transport of the sugar glucose from blood into muscles and other tissues (i.e. sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose starts to rise, resulting in diabetes. Insulin resistance ranges from normal (insulin sensitive) to insulin resistant (IR).

An "insulin resistance disorder," as used herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis.

As used herein, the term "biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, the biomarkers demonstrate a correlation with pre-diabetes, or particular levels of pre-diabetes. The range of possible correlations is between negative (−) 1 and positive (+) 1. A result of negative (−) 1 means a perfect negative correlation and a positive (+) 1 means a perfect positive correlation, and 0 means no correlation at all. A "substantial positive correlation" refers to a biomarker having a correlation from +0.25 to +1.0 with a disorder or with a clinical measurement (e.g., Rd), while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement (e.g., Rd), while a "significant negative correlation" refers to a correlation to a disorder of from −0.5 to −1.0 with a given disorder or clinical measurement.

As used herein, the term "metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

As used herein, the term "metabolic profile" or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

As used herein, the term "level" of one or more biomarkers means the absolute or relative amount or concentration of the biomarker in the sample.

As used herein, the term "sample" or "biological sample" or "specimen" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, adipose tissue, aortic tissue, liver tissue, blood, blood plasma, serum, or urine.

"Impaired fasting glucose (IFG)" and "impaired glucose tolerance (IGT)" are clinical definitions of "pre-diabetes". IFG is defined as a fasting blood glucose concentration of 100-125 mg/dL. IGT is defined as a postprandial (after eating) blood glucose concentration of 140-199 mg/dL. It is known that IFG and IGT do not always detect the same pre-diabetic populations.

Between the two populations there is approximately a 60% overlap observed. Fasting plasma glucose levels are a more efficient means of inferring a patient's pancreatic function, or insulin secretion, whereas postprandial glucose levels are more frequently associated with inferring levels of insulin sensitivity or resistance. IGT is known to identify a greater percentage of the pre-diabetic population compared to IFG. The IFG condition is associated with lower insulin secretion, whereas the IGT condition is known to be strongly associated with insulin resistance. Numerous studies have been carried out that demonstrate that IGT individuals with normal FPG values are at increased risk for cardiovascular disease. Patients with normal FPG values may have abnormal postprandial glucose values and are often unaware of their risk for pre-diabetes, diabetes, and cardiovascular disease.

"Fasting plasma glucose (FPG) test" is a simple test measuring blood glucose levels after an 8 hour fast. According to the ADA, blood glucose concentration of 100-125 mg/dL is considered IFG and defines pre-diabetes whereas ≥126 mg/dL defines diabetes. As stated by the ADA, FPG is the preferred test to diagnose diabetes and pre-diabetes due to its ease of use, patient acceptability, lower cost, and relative reproducibility. The weakness in the FPG test is that patients are quite advanced toward type 2 diabetes before fasting glucose levels change.

"Oral glucose tolerance test (OGTT)", a dynamic measurement of glucose, is a postprandial measurement of a patient's blood glucose levels after oral ingestion of a 75 g glucose drink. Traditional measurements include a fasting blood sample at the beginning of the test, a one hour time point blood sample, and a 2 hour time point blood sample. A patient's blood glucose concentration at the 2 hour time point defines the level of glucose tolerance: Normal glucose tolerance (NGT)≤140 mg/dL blood glucose; Impaired glucose tolerance (IGT)=140-199 mg/dL blood glucose; Diabetes ≥200 mg/dL blood glucose. As stated by the ADA, even though the OGTT is known to be more sensitive and specific at diagnosing pre-diabetes and diabetes, it is not recommended for routine clinical use because of its poor reproducibility and difficulty to perform in practice.

"Hemoglobin A1c (HbA1c) test", also known as "A1C test" or "glycohemoglobin test", is a blood test that provides information about a person's average levels of blood glucose, also called blood sugar, over the past 3 months. The A1C test is based on the attachment of glucose to hemoglobin, the protein in red blood cells that carries oxygen. In the body, red blood cells are constantly forming and dying, but typically they live for about 3 months. Thus the A1C test reflects the average of a person's blood glucose levels over the past 3 months. The A1C test result is reported as a percentage. The higher the percentage, the higher a person's blood glucose levels have been. A normal A1C level is below 5.7 percent. An A1C level between 5.7 and 6.4 percent is considered "prediabetes". A level of 6.5 percent or higher indicates diabetes.

The present invention can be understood more fully by reference to the following detailed description and examples, which are intended to exemplify non-limiting embodiments of the invention.

Compounds and Compositions

The present invention provides novel compounds, compositions and their use in diagnostic methods and treatment methods.

In a first embodiment, the compound of the present invention is represented by formula (I):

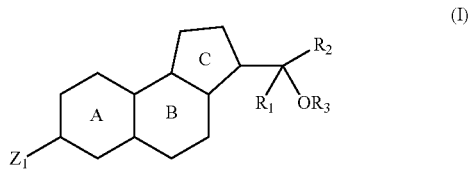

or a salt (e.g., a pharmaceutically acceptable salt) thereof, wherein the variables are as described above.

In a second embodiment, the compound of the present invention is represented by formula (II):

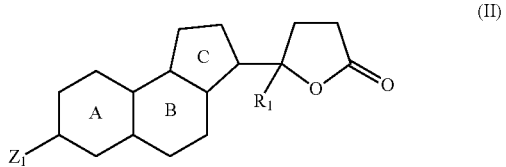

or a salt (e.g., a pharmaceutically salt) thereof, wherein $Z_1$ is $-OR^a$, $-OSO_3H$, $-OPO(OH)_2$, $-OC(=O)R^b$, or $-OC(=O)NR^cR^d$ and the remaining variables are as described above in the first embodiment.

In a third embodiment, the compound of the present invention is represented by formula

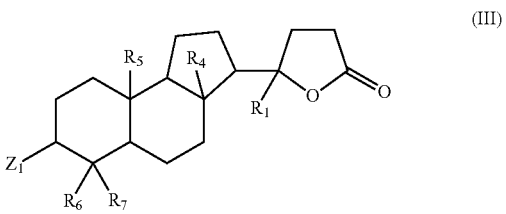

or a salt (e.g., a pharmaceutically acceptable salt) thereof, wherein:

$R_4$, $R_5$, $R_6$ and $R_7$ are each independently selected from the group consisting of —H, halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$)alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl;

wherein each of (C$_1$-C$_6$)alkyl, (C$_2$-C$_6$)alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl groups described above is optionally substituted with 1 to 5 substituents independently selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, halo(C$_1$-C$_6$)alkyl and hydroxyl(C$_1$-C$_6$)alkyl and the remaining variable are as described above in the first or second embodiment.

In a fourth embodiment, for compounds represented by formulas (I), (II) and (III), $R_1$ is a (C$_1$-C$_6$)alkyl and the remaining variables are as described above in the first, second or third embodiment.

In a fifth embodiment, for compounds represented by formulas (I), (II) and (III), $R_1$ is methyl and the remainder of the variables are as described above in the first, second or third embodiment.

In a sixth embodiment, for compounds represented by formula (III), $R_4$, $R_5$, $R_6$ and $R_7$ are each independently —H, halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, halo(C$_1$-C$_6$)alkyl and (C$_1$-C$_3$)alkoxy(C$_1$-C$_6$)alkyl and the remaining variables are as described above in the first, second, third, fourth or fifth embodiment.

In a seventh embodiment, for compounds represented by formula (III), $R_4$, $R_5$, $R_6$ and $R_7$ are each independently (C$_1$-C$_6$)alkyl or halo(C$_1$-C$_6$)alkyl and the remaining variables are as described above in the first, second, third, fourth or fifth embodiment.

In an eighth embodiment, for compounds represented by formula (III), $R_4$, $R_5$, $R_6$ and $R_7$ are each methyl and the remainder of the variables are as described above in the first, second, third, fourth or fifth embodiment.

In a ninth embodiment, the compound of the present invention is:

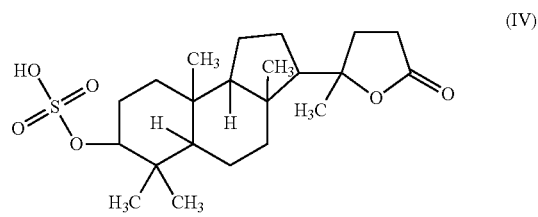

or a salt (e.g., a pharmaceutically acceptable salt) thereof.

In a tenth embodiment, the compound of the present invention is:

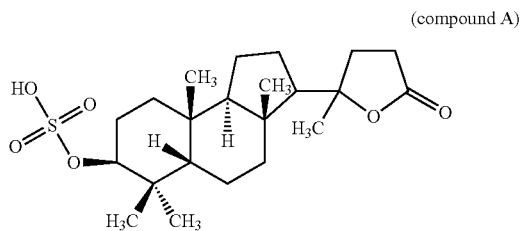

(compound A)

or a pharmaceutically acceptable salt thereof.

In a eleventh embodiment, the compound of the present invention is:

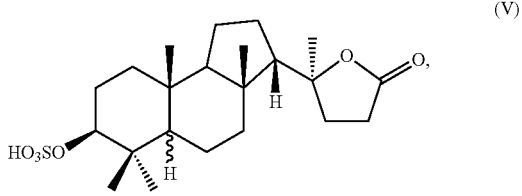

(V)

or a salt (e.g., a pharmaceutically acceptable salt) thereof.

In a twelfth embodiment, the compound of the present invention is:

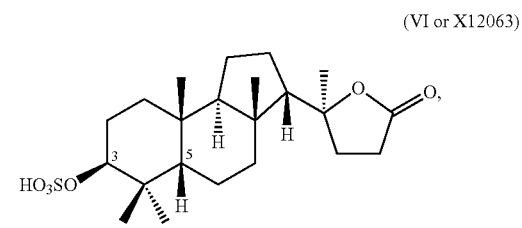

(VI or X12063)

or a salt (e.g., a pharmaceutically acceptable salt) thereof.

In a thirteenth embodiment, the compound of the present invention is:

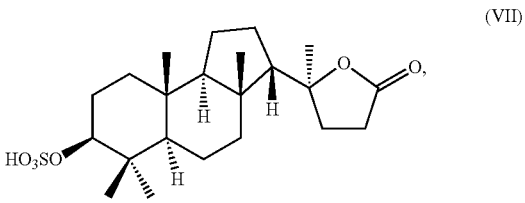

(VII)

or a salt (e.g., a pharmaceutically acceptable salt) thereof.

In various embodiments, the compound of the present invention described herein (e.g., compounds represented by formula (V), (VI), or (VII) or compound A or a salt thereof) are at least 60% optically pure, at least 70% optically pure, at least 80% optically pure, at least 90% optically pure, at least 95% optically pure, or at least 99% optically pure.

In various embodiments, the compound of the present invention described herein (e.g., compounds represented by formula (I), (II), (III), (IV), (V), (VI), or (VII) or compound A or a salt thereof) are substantially free of impurities.

In various embodiments, the compound of the present invention described herein (e.g., compounds represented by formula (I), (II), (III), (IV), (V), (VI), or (VII) or compound A or a salt thereof) are at least 60% pure, at least 70% pure, at least 80% pure, at least 90% pure, at least 95% pure or at least 99% pure.

The compounds described above, such as compounds of formulas (I), (II), (III), (IV), (V), (VI), or (VII) or compound A or a salt (e.g., a pharmaceutically acceptable salt) thereof, can be used in any of the methods described herein.

In a particular embodiment, the present invention provides a pharmaceutical composition comprising a pharmaceutically acceptable carrier or diluent and a compound disclosed herein (e.g., a compound represented by formula (I), (II), (III), (IV), (V), (VI), or (VII) or compound A or a salt (e.g., a pharmaceutically acceptable salt) thereof).

In one embodiment, a composition of the present invention contains more than about 80% by weight, more preferably more than about 90% by weight, even more preferably more than about 95% by weight, and most preferably more than about 97% by weight of the compound described herein (e.g., compound of formula (I), (II), (III), (IV), (V), (VI), or (VII) or compound A or a salt (e.g., a pharmaceutically acceptable salt) thereof).

In one embodiment, the pharmaceutical compositions described herein contain at least about 80%, 85%, 90%, 95%, 98%, or 99% by weight of the compound described herein.

"Pharmaceutically acceptable carrier" means compounds and compositions that are of sufficient purity and quality for use in the formulation of a composition of the invention and that, when appropriately administered to an animal or human, do not produce an adverse reaction.

In certain embodiments, the compounds described herein is radiolabeled, such as with tritium ($^3$H) or carbon 14 ($^{14}$C). Any suitable methods for radiolabelling the compounds of the present invention can be used.

Also included in the present invention is antibodies or antibodies fragment that specifically binds to the compound described herein (e.g. compound of formula (I), (II), (III), (IV), (V), (VI), or (VII) or compound A or a salt (e.g., a pharmaceutically acceptable salt) thereof). Methods for generating antibodies that specifically binds to small molecules are known in the art. Antibody derivatives, such as a polypeptide comprising the $V_H$ and $V_L$ sequences of the antibody described above are also included. In certain embodiment, the polypeptide is a fusion protein. The present invention also includes cells for producing the antibodies or antibody fragments and the antibody derivatives described herein.

Methods

The present invention includes diagnostic methods for diagnosing, monitoring and treating insulin resistance, a metabolic disorder, diabetes and pre-diabetes in a subject.

In a 1$^{st}$ embodiment, the present invention provides a method for diagnosing a disease or disorder selected from the group consisting of insulin resistance, a metabolic disorder, diabetes and pre-diabetes in a subject comprising the steps of:

(1) determining the level of a compound of the present invention described above (e.g., a compound represented by formula (I):

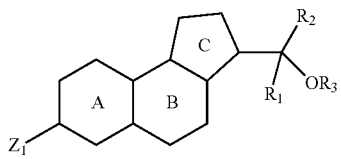
(I)

or a salt thereof), in a biological sample from the subject, wherein the variables are as described above; and (2) comparing the level of the compound in the biological sample with the level of the compound in a normal control sample, wherein an altered level of the compound in the biological sample is indicative of the disease or disorder in the subject.

In one embodiment, the method for diagnosing a disease or disorder described above further comprises treating the subject with an effective therapy suitable for treating the disease or disorder when an altered level of the compound is present in the biological sample as compared to the level of the compound in the normal control sample.

In a $2^{nd}$ embodiment, the present invention provides a method for monitoring the progression or regression of a disease or disorder selected from the group consisting of insulin resistance, a metabolic disorder, diabetes and pre-diabetes in a subject comprising the steps of:

(1) determining the level of a compound of the present invention described above (e.g., a compound represented by formula (I):

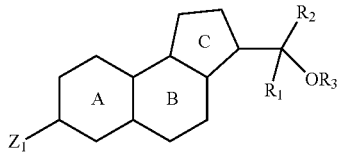
(I)

or a salt thereof), in a first biological sample obtained at a first time from the subject, wherein the variables are as described above;

(2) determining the level of the compound in a second biological sample obtained from the subject at a second time, wherein the second time is later than the first time; and (3) comparing the level of the compound in the second biological sample with the level of the compound in the first biological sample, wherein a change in the level of the compound is indicative of progression or regression of the disease in the subject.

In one embodiment, the method for monitoring the progression or regression of a disease or disorder described above further comprises treating the subject with an effective therapy suitable for treating the disease or disorder when regression of the disease is observed.

A $3^{rd}$ embodiment of the invention is a method of monitoring the efficacy of insulin resistance treatment, a metabolic disorder treatment, diabetes treatment or pre-diabetes treatment in a subject, the method comprising the steps of:

(1) determining the level of a compound of formula (I):

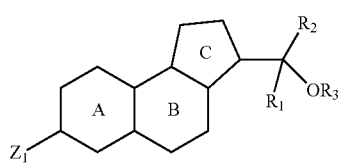
(I)

or a salt thereof, in a biological sample from the subject;

(2) treating the subject with an effective therapy for insulin resistance, a metabolic disorder, diabetes or pre-diabetes;

(3) analyzing a second biological sample from the subject to determine the level of the compound of formula (I), wherein the second sample obtained from the subject at a second time point after treatment; and (4) comparing the level of the compound of formula (I) in the first sample to the level of the compound of formula (I) in the second sample to assess the efficacy of the treatment for treating insulin resistance, a metabolic disorder, diabetes or pre-diabetes.

In various embodiments, for methods described above (e.g., the method described in the $1^{st}$, $2^{nd}$ or $3^{rd}$ embodiment), the compound of formula (I) is represented by formula (II), (III) or (IV) or compound A or a salt thereof. Alternatively, for methods described above, the compound of formula (VI) is X12063 described above or a salt thereof.

In a $4^{th}$ embodiment, the present invention provides a method for diagnosing a disease or disorder selected from the group consisting of insulin resistance, a metabolic disorder, diabetes and pre-diabetes in a subject comprising: determining the level of a compound represented by formula (IV):

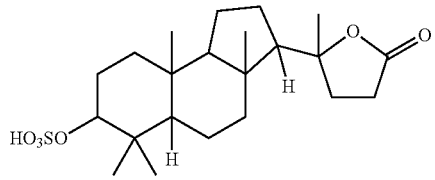

or a salt thereof, in a biological sample from the subject, wherein an elevated level of the compound in the biological sample as compared to the level of the compound in a normal control sample is indicative of the disease or disorder in the subject. In one embodiment, the level of the compound is determined by chromatography, mass spectrometry, enzyme-linked immunosorbent assay (ELISA), antibody linkage, or other immunochemical methods.

In a $5^{th}$ embodiment, the present invention provides a method for diagnosing a disease or disorder selected from the group consisting of insulin resistance, a metabolic disorder, diabetes and pre-diabetes in a subject comprising: determining the level of a compound represented by formula (VI):

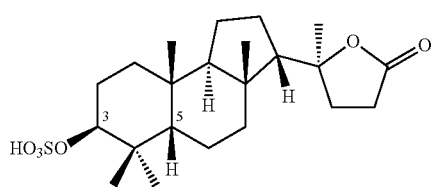

or a salt thereof, in a biological sample from the subject, wherein an elevated level of the compound in the biological sample as compared to the level of the compound in a normal control sample is indicative of the disease or disorder in the subject. In one embodiment, the level of the compound is determined by chromatography, mass spectrometry, enzyme-linked immunosorbent assay (ELISA), antibody linkage, or other immunochemical methods.

As used herein, a "normal control sample" refers to a sample from a subject or a subject itself that does not have the disease or disorder, such as insulin resistance, a metabolic disorder, diabetes and pre-diabetes.

In certain embodiments, the method described above (e.g., the method described in the $4^{th}$ or $5^{th}$ embodiment) further comprises treating the subject with an effective therapy suitable for treating the disease or disorder when an elevated level of the compound is present in the biological sample as compared to the level of the compound in the normal control sample.

In a $6^{th}$ embodiment, the present invention provides a method for monitoring the progression or regression of a disease or disorder selected from the group consisting of insulin resistance, a metabolic disorder, diabetes and pre-diabetes in a subject comprising:

(1) determining the level of a compound represented by formula (IV):

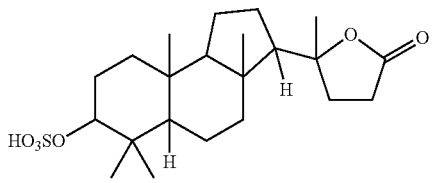

or a salt thereof, in a biological sample from the subject, (2) determining the level of the compound in a second biological sample obtained from the subject at a second time, wherein the second time is later than the first time;

wherein a change in the level of the compound is indicative of progression or regression of the disease in the subject and wherein the level of the compound is determined by chromatography, mass spectrometry, enzyme-linked immunosorbent assay (ELISA), antibody linkage, or other immunochemical methods. In one embodiment, an increase in the level of the compound is indicative of progression of the disease.

In a $7^{th}$ embodiment, the present invention provides a method for monitoring the progression or regression of a disease or disorder selected from the group consisting of insulin resistance, a metabolic disorder, diabetes and pre-diabetes in a subject comprising:

(1) determining the level of a compound represented by formula (VI):

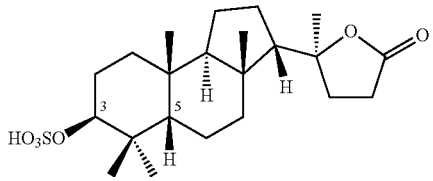

or a salt thereof, in a biological sample from the subject, (2) determining the level of the compound in a second biological sample obtained from the subject at a second time, wherein the second time is later than the first time;

wherein a change in the level of the compound is indicative of progression or regression of the disease in the subject and wherein the level of the compound is determined by chromatography, mass spectrometry, enzyme-linked immunosorbent assay (ELISA), antibody linkage, or other immunochemical methods. In one embodiment, an increase in the level of the compound is indicative of progression of the disease.

In certain embodiments, the method described above (e.g., the method described in the $6^{th}$ or $7^{th}$ embodiment) further comprises treating the subject with an effective therapy suitable for treating the disease or disorder.

In a $8^{th}$ embodiment, the present invention provides a method of monitoring the efficacy of a therapy for treating insulin resistance, a metabolic disorder, diabetes or pre-diabetes in a subject, the method comprising the steps of:

(1) determining the level of a compound represented by formula (IV):

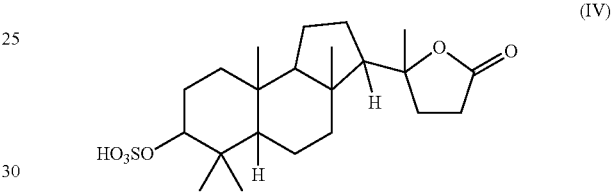

or a salt thereof, in a biological sample from the subject;

(2) treating the subject with the therapy for insulin resistance, a metabolic disorder, diabetes or pre-diabetes;

(3) analyzing a second biological sample from the subject to determine the level of the compound, wherein the second sample is obtained from the subject at a time point after the treatment; and (4) comparing the level of the compound in the first sample to the level of the compound in the second sample to assess the efficacy of the treatment for treating insulin resistance, a metabolic disorder, diabetes or pre-diabetes, wherein the level of the compound is determined by chromatography, mass spectrometry, enzyme-linked immunosorbent assay (ELISA), antibody linkage, or other immunochemical methods. In one embodiment, a decrease in the level of the compound in the second sample as compared in the first sample indicates that the therapy used is effective in treating the subject.

In a $9^{th}$ embodiment, the present invention provides a method of monitoring the efficacy of a therapy for treating insulin resistance, a metabolic disorder, diabetes or pre-diabetes in a subject, the method comprising the steps of:

(1) determining the level of a compound represented by formula (VI):

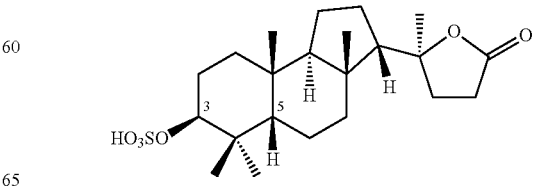

or a salt thereof, in a biological sample from the subject;

(2) treating the subject with the therapy for insulin resistance, a metabolic disorder, diabetes or pre-diabetes;

(3) analyzing a second biological sample from the subject to determine the level of the compound, wherein the second sample is obtained from the subject at a time point after the treatment; and (4) comparing the level of the compound in the first sample to the level of the compound in the second sample to assess the efficacy of the treatment for treating insulin resistance, a metabolic disorder, diabetes or pre-diabetes, wherein the level of the compound is determined by chromatography, mass spectrometry, enzyme-linked immunosorbent assay (ELISA), antibody linkage, or other immunochemical methods. In one embodiment, a decrease in the level of the compound in the second sample as compared in the first sample indicates that the therapy used is effective in treating the subject.

In various embodiments, for methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the level of the compound is determined by chromatography, mass spectrometry, ELISA, antibody linkage or enzymatic reactions or assays or other immunochemical methods.

In one embodiment, the level of the compound is determined using LC-MS/MS by comparison of the peak area of the product ion of the compound against the peak area of the product ion of an internal standard measured by tandem liquid chromatography-mass spectrometry (LC-MS/MS) or by comparison of the peak area of the product ion of the compound in a diseased patients sample compared to the peak area of the product ion of the compound in a normal sample or population measured by tandem liquid chromatography-mass spectrometry (LC-MS/MS).

In various embodiments, for methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the effective therapy involves the use of an effective therapeutic agent suitable for treating the disease or disorder.

Therapeutic agent suitable for use in methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment) include, but are not limited to, antidiabetic and antiobesity drugs. In a particular embodiment, for methods described herein, the therapeutic agents include, but are not limited to, metformin, pioglitazone, rosiglitazone, acarbose, tetrahydrolipstatin, phentermine/topiramate, bupropion/naltrexone, lorcaserin, liraglutide, and canagliflozin.

In various embodiments, for methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the effective therapy comprises a lifestyle modification of the subject. In a particular embodiment, the lifestyle modification is selected from the group consisting of dietary modification and/or an increase in activity or exercise.

Dietary modification may include, for example, limiting calories intake, serving sizes, sugar and starchy carbohydrates content and/or choosing foods that are low in fat and calories and high in fiber.

In various embodiments, for methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the method further comprises analyzing the biological sample to determine the level of one or more additional biomarkers other than the compound of the present invention (e.g., compounds of formula (I), (II), (III), (IV), (V), (VI), or (VII) or a salt (e.g., a pharmaceutically acceptable salt) thereof)), wherein the one or more additional biomarkers are related to the disease or disorder.

Biomarkers for use in the methods disclosed herein may be obtained from any source of biomarkers related to pre-diabetes and/or type-2 diabetes. In a particular embodiment, biomarkers for use in methods described herein were discovered using metabolomic profiling techniques. Such metabolomic profiling techniques are described in more detail in U.S. Pat. Nos. 7,005,255 and 7,329,489 and U.S. patent application Ser. No. 11/357,732 (Publication No. 2007/0026389), Ser. No. 11/301,077 (Publication No. 2006/0134676), Ser. No. 11/301,078 (Publication No. 2006/0134677), Ser. No. 11/301,079 (Publication No. 2006/0134678), and Ser. No. 11/405,033 (Publication No. US 2007/0072203), the entire contents of which are hereby incorporated herein by reference.

In a particular embodiment, for methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the additional biomarker is selected from the group consisting of 2-hydroxybutyrate (AHB), linoleoyl lysophosphatidylcholine (LGPC), oleate, 4-methyl-2-oxo-pentanoate, panthothenate (vitamin B5), beta-hydroxybutyrate (BHBA), and serine and optionally one or more additional biomarkers selected from the group consisting of 3-methyl-2-oxo-butyric acid, alpha-ketoglutarate, creatine, glycine, isoleucine, leucine, leucine, oleoyl lysophosphatidylcholine, phenylalanine, trigonelline, tyrosine, valine, hydrocinnamic acid, xanthine, mannose, 3-methyl-2-oxovalerate, glycerolphosphorylcholine, adrenate, 3-methyl-2-oxo-pentanoate, 2-methylsuccinate, 1-octadecanol, 2-aminoadipate, 3-hydroxyisobutyrate, alpha-tocopherol, arginine, betaine, decanoylcarnitine, docosatetraenoic acid, glutamic acid, linoleic acid, linolenic acid, margaric acid, N-acetylglycine, octanoylcarnitine, palmitate, palmitoleic acid, palmitoyl lysophosphatidylcholine, stearate, threonine, and tryptophan.

In another embodiment, for the methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the biomarker 2-methyl succinate is selected. Plasma levels of 2-methylsuccinate were 4.21-fold higher in type 2 diabetic subjects compared to non-diabetic subjects in a cohort consisting of age and sex-matched Japanese subjects. Classification analysis using Random Forest for metabolites that discriminated between diabetics and non-diabetics indicated that 2-methyl succinate had the highest ranking out of 1189 metabolites measured in the experiment.

In one embodiment, for the methods described herein (e.g., the method described in the $1^{st}$, $2^{nd}$, $3^{rd}$, $4^{th}$, $5^{th}$, $6^{th}$, $7^{th}$, $8^{th}$, or $9^{th}$ embodiment), the method comprises analyzing the biological sample to determine the level of the compound of the present invention (e.g., compounds of formula (I), (II) or (III), (IV), (V), (VI), or (VII), or a salt (e.g., a pharmaceutically acceptable salt) thereof)), and the level of 2-hydroxybutyrate (AHB) and linoleoyl lysophosphatidylcholine (LGPC). Optionally, the method can further comprise analyzing the biological sample to determine the level of one or more biomarkers selected from the group consisting of 3-methyl-2-oxo-butyric acid, alpha-ketoglutarate, creatine, glycine, isoleucine, leucine, oleoyl lysophosphatidylcholine, phenylalanine, trigonelline, tyrosine, valine, hydrocinnamic acid, xanthine, mannose, 3-methyl-2-oxovalerate, glycerolphosphorylcholine, adrenate, 3-methyl-2-oxo-pentanoate, 2-methylsuccinate, 1-octadecanol, 2-aminoadipate, 3-hydroxyisobutyrate, alpha-tocopherol, arginine, betaine, decanoylcarnitine, docosatetraenoic acid, glutamic acid, linoleic acid, linolenic acid, margaric acid, N-acetylglycine, octanoylcarnitine, palmitate, palmitoleic acid, palmitoyl lysophosphatidylcholine, stearate, threonine, and tryptophan.

In certain embodiments, the method described above (e.g., the method described in the 1$^{st}$, 2$^{nd}$, 3$^{rd}$, 4$^{th}$, 5$^{th}$, 6$^{th}$, 7$^{th}$, 8$^{th}$, or 9$^{th}$ embodiment) further comprises using the determined level of the compound and the determined level(s) of the one or more additional biomarkers in a mathematical model to classify a subject as having insulin resistance, a metabolic disorder, diabetes, pre-diabetes, NGT, IGT, or type-2 diabetes.

Any suitable method may be used to analyze the biological sample in order to determine the level(s) of one or more biomarkers in the sample. Suitable methods include, but are not limited to, chromatography (e.g., HPLC, gas chromatography, liquid chromatography), mass spectrometry (e.g., MS, MS/MS), enzyme-linked immunosorbent assay (ELISA), antibody linkage, other immunochemical techniques, and combinations thereof. In an embodiment, the biological sample is analyzed using LC-MS/MS to determine the level of the biomarker.

Further, the level(s) of one or more biomarkers may be measured indirectly, for example, by using an assay that measures the level of a compound (or compounds) that correlates with the level of the biomarker(s) that are desired to be measured.

When a method of the present invention described herein (e.g., the method described in the 1$^{st}$, 2$^{rd}$, 3$^{rd}$, 4$^{th}$, 5$^{th}$, 6$^{th}$, 7$^{th}$, 8$^{th}$, or 9$^{th}$ embodiment) is used in the diagnosis and monitoring of a disease or condition, or aiding in the diagnosis and monitoring of a disease or condition, or monitoring the efficacy of a therapy for treating a disease or condition, such as insulin resistance, a metabolic disorder, diabetes and pre-diabetes, the results of the method may be used along with other methods (or the results thereof) useful in the clinical determination of whether a subject has a given disease or condition. Methods useful in the clinical determination of whether a subject has a disease or condition such as insulin resistance, a metabolic disorder, diabetes and pre-diabetes, are known in the art. For example, methods useful in the clinical determination of whether a subject has pre-diabetes include, for example, age determination, gender determination, family history determination, glucose disposal rates (Rd) measurements, body weight measurements, waist circumference measurements, BMI determinations, Peptide YY measurements, Hemoglobin A1C measurements, fasting glucose glucose measurements, fasting insulin measurements, pro-insulin measurements, C-peptide measurements, C-reactive protein measurements, hemoglobin A1c (HbA1c or A1c) measurements, LDL-C measurements, HDL-C measurements, free fatty acid (FFA) measurements, 1,5-Ag (Glycomark) measurements, triglycerides measurements, and the like.

The present invention also provides methods of treating insulin resistance, a metabolic disorder, diabetes and pre-diabetes in a subject.

In a 10$^{th}$ embodiment, the present invention provides a method of treating a disease or disorder selected from the group consisting of insulin resistance, a metabolic disorder, diabetes and pre-diabetes in a subject comprising administrating an effective therapy suitable for treating the disease or disorder to the subject, wherein the subject has an elevated level of a compound described herein (e.g., compound of formula (I), (II), (III), (IV), (V), (VI) or compound A).

In a 11$^{th}$ embodiment, the present invention provides a method of treating a disease or disorder selected from the group consisting of insulin resistance, a metabolic disorder, diabetes and pre-diabetes in a subject comprising:

(1) determining the level of a compound described herein (e.g., compound of formula (I), (II), (III), (IV), (V), (VI) or compound A) or a salt thereof, in a biological sample from the subject by chromatography, mass spectrometry, enzyme-linked immunosorbent assay (ELISA), or other immunochemical methods; and 2) administrating an effective therapy suitable for treating the disease or disorder to the subject when the subject has an elevated level of the compound as compared to the level of the compound in a normal control sample.

In a 12$^{th}$ embodiment, the present invention provides a method of treating a disease or disorder selected from the group consisting of insulin resistance, a metabolic disorder, diabetes and pre-diabetes in a subject comprising administrating an effective therapy suitable for treating the disease or disorder to the subject, wherein the subject has an elevated level of a compound represented by the following formula:

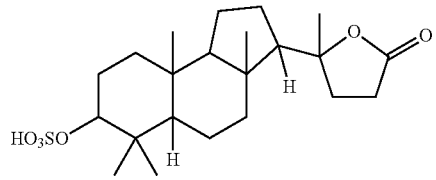

or a salt thereof, as compared to a normal control subject.

In a 13$^{th}$ embodiment, the present invention provides a method of treating a disease or disorder selected from the group consisting of insulin resistance, a metabolic disorder, diabetes and pre-diabetes in a subject comprising administrating an effective therapy suitable for treating the disease or disorder to the subject, wherein the subject has an elevated level of a compound represented by the following formula:

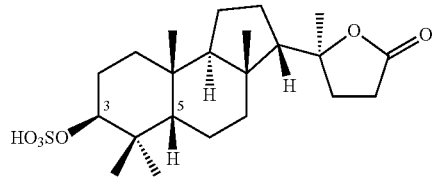

or a salt thereof, as compared to a normal control subject.

As used herein, a "normal control subject" refers to a subject that does not have the disease or disorder, such as insulin resistance, a metabolic disorder, diabetes and pre-diabetes.

In certain embodiments, the level of the compound is determined by obtaining a biological sample from the subject and determining the level of the compound by chromatography, mass spectrometry, enzyme-linked immunosorbent assay (ELISA), antibody linkage, or other immunochemical methods.

In a 14$^{th}$ embodiment, the present invention provides a method of treating a disease or disorder selected from the group consisting of insulin resistance, a metabolic disorder, diabetes and pre-diabetes in a subject comprising:

(1) determining the level of a compound represented by the following formula:

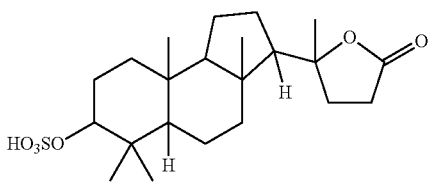

or a salt thereof, in a biological sample from the subject by chromatography, mass spectrometry, enzyme-linked immunosorbent assay (ELISA), or other immunochemical methods; and 2) administrating an effective therapy suitable for treating the disease or disorder to the subject when the subject has an elevated level of the compound as compared to the level of the compound in a normal control sample.

In a 15$^{th}$ embodiment, the present invention provides a method of treating a disease or disorder selected from the group consisting of insulin resistance, a metabolic disorder, diabetes and pre-diabetes in a subject comprising:

(1) determining the level of a compound represented by the following formula:

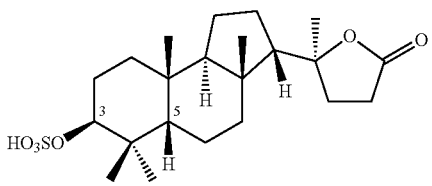

or a salt thereof, in a biological sample from the subject by chromatography, mass spectrometry, enzyme-linked immunosorbent assay (ELISA), or other immunochemical methods; and 2) administrating an effective therapy suitable for treating the disease or disorder to the subject when the subject has an elevated level of the compound as compared to the level of the compound in a normal control sample.

In certain embodiments, for methods described herein (e.g., the method described in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$ or 15$^{th}$ embodiment), the disease or disorder is type 2 diabetes or pre-diabetes. In one embodiment, the prediabetes is characterized with isolated impaired fasting glucose (IFG), isolated impaired glucose tolerance (IGT), combination of IFG and IGT, high hemoglobin A1C level, or a combination thereof. In one embodiment, the prediabetes is characterized with a hemoglobin A1C level of between 5.7% and 6.4%.

Kits

The present invention also includes kits for diagnosing and/or monitoring a disease or disorder selected from the group consisting of insulin resistance, a metabolic disorder, diabetes and pre-diabetes in a subject.

In certain embodiments, the kit of the present invention can comprise a labeled compound or agent capable of detecting the relevant small molecule (such as X12063) in a biological sample and means for determining the amount of the relevant small molecule in the sample (e.g., an antibody against the relevant small molecule another molecular or chemical sensor).

The kit may also comprise, e.g., a buffering agent, a preservative, or a stabilizing agent. The kit may also contain a control sample or a series of control samples which can be assayed and compared to the test sample. Each component of the kit is usually enclosed within an individual container and all of the various containers are within a single package along with instructions for determining whether the tested subject is suffering from or is at risk of developing a disorder associated with the relevant small molecule.

In one embodiment, the kit comprises a compound of the present invention described above (e.g., a compound represented by formula (I):

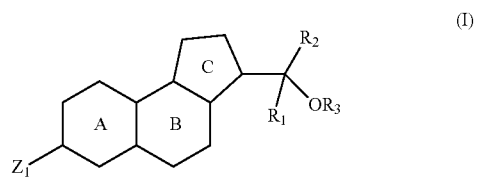

or a salt thereof, wherein the variables are as described above), and instructions for diagnosing and monitoring a disease or disorder selected from the group consisting of insulin resistance, a metabolic disorder, diabetes and pre-diabetes in a subject based on the level of the compound detected in a biological sample from the subject. In certain embodiments, the compound of formula (I) is represented by formula (II), (III), (IV), (V) or (VI) or compound A, or a salt thereof.

In another embodiment, the kit comprises a compound of formula (IV):

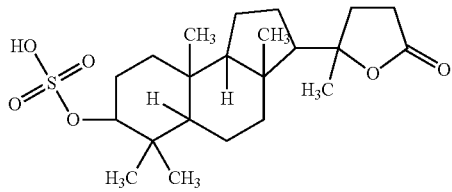

or a salt thereof, and instructions for diagnosing and/or monitoring a disease or disorder selected from the group consisting of insulin resistance, a metabolic disorder, diabetes and pre-diabetes in a subject based on the level of the compound detected in a biological sample from the subject.

In another embodiment, the kit comprises a compound of formula (VI):

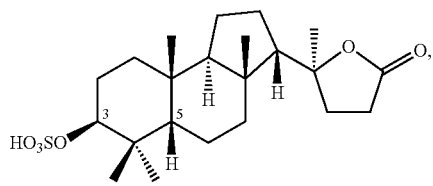

or a salt thereof, and instructions for diagnosing and/or monitoring a disease or disorder selected from the group consisting of insulin resistance, a metabolic disorder, diabetes and pre-diabetes in a subject based on the level of the compound detected in a biological sample from the subject.

In certain embodiments, the compound of formula (VI) is radiolabeled, for example, with tritium ($^3$H) or carbon 14 ($^{14}$C).

In another embodiment, the kit described above comprises one or more additional biomarkers other than the compound, wherein the one or more additional biomarkers are related to the disease or disorder. Any biomarkers described herein can be used in the kits of the present invention.

In various embodiments, for kits described herein, the one or more additional biomarkers are selected from 2-hydroxybutyrate (AHB), linoleoyl lysophosphatidylcholine (LGPC), oleate, 4-methyl-2-oxo-pentanoate, panthothenate (vitamin B5), beta-hydroxybutyrate (BHBA), and serine and optionally one or more additional biomarkers selected from the group consisting 3-methyl-2-oxo-butyric acid, alpha-ketoglutarate, creatine, glycine, isoleucine, leucine, leucine, oleoyl lysophosphatidylcholine, phenylalanine, trigonelline, tyrosine, valine, hydrocinnamic acid, xanthine, mannose, 3-methyl-2-oxovalerate, glycerolphosphorylcholine, adrenate, 3-methyl-2-oxo-pentanoate, 2-methylsuccinate, 1-octadecanol, 2-aminoadipate, 3-hydroxyisobutyrate, alpha-tocopherol, arginine, betaine, decanoylcarnitine, docosatetraenoic acid, glutamic acid, linoleic acid, linolenic acid, margaric acid, N-acetylglycine, octanoylcarnitine, palmitate, palmitoleic acid, palmitoyl lysophosphatidylcholine, stearate, threonine, and tryptophan and combinations thereof.

In certain embodiment, the kits of the present invention comprises a compound of the present invention described above, 2-hydroxybutyrate (AHB) and linoleoyl lysophosphatidylcholine (LGPC) as one or more additional biomarkers.

Such biomarkers allow subjects to be classified as insulin resistant, insulin impaired, or insulin sensitive. In a particular embodiment, the biomarkers for use in methods and kits described herein include, 2-hydroxybutyrate, linoleoyllysophosphatidylcholine, oleate, serine, glycine, tyrosine, alpha-ketoglutarate, pantothenate, 3-hydroxybutyrate, and 4-methyl-2-oxo-pentanoate.

In certain embodiments, the kits of the present invention comprise an internal standard for chromatography that is not compound of formula (VI) (i.e., X12063). The internal standard is for determining the level of compound of formula (IV) or (VI) in a biological sample of a test subject.

In one embodiment, the internal standard has the same chromatographic elution profile (such as liquid chromatography elution profile) as the compound of formula (IV) or (VI).

In one embodiment, the internal standard for determining the level of the compound of formula (IV) is the compound of formula (VII). Accordingly, in certain embodiments, the kits of the present invention comprises a compound represented by the following formula:

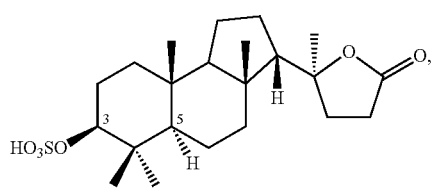

(VII)

or a salt thereof, and instructions for diagnosing and/or monitoring a disease or disorder selected from the group consisting of insulin resistance, a metabolic disorder, diabetes and pre-diabetes in a subject based on the level of the compound of formula (IV) detected in a biological sample from the subject.

In one embodiment, the internal standard for determining the level of the compound of formula (VI) is the compound of formula (VII). Accordingly, in certain embodiments, the kits of the present invention comprises a compound represented by the following formula:

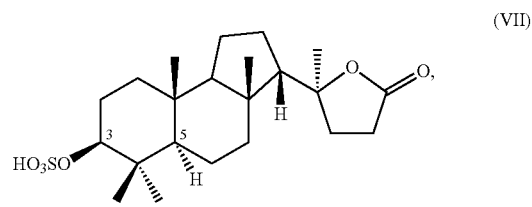

(VII)

or a salt thereof, and instructions for diagnosing and/or monitoring a disease or disorder selected from the group consisting of insulin resistance, a metabolic disorder, diabetes and pre-diabetes in a subject based on the level of the compound of formula (VI) detected in a biological sample from the subject.

In certain embodiment, the compound of formula (VII) is radiolabeled, for example, with tritium ($^3$H) or carbon 14 ($^{14}$C).

In certain embodiments, the kits described herein is for diagnosing and/or monitoring type 2 diabetes or prediabetes in a subject. In one embodiment, the prediabetes is characterized with isolated impaired fasting glucose (IFG), isolated impaired glucose tolerance (IGT), combination of IFG and IGT, high hemoglobin A1C level, or a combination thereof. In one embodiment, the prediabetes is characterized with a hemoglobin A1C level of between 5.7% and 6.4%.

Methods of Preparation

One can refer to the following references for suitable methods of synthesis as described in March, *Advanced Organic Chemistry*, 3rd edition, John Wiley & Sons, 1985 or Greene and Wuts *Protective groups in organic synthesis* 2$^{nd}$ edition, John Wiley & sons 1991 and as in Richard Larock, *comprehensive organic transformations*, 4$^{th}$ edition, VCH publishers Inc, 1989.

In certain embodiments, the compounds of the present invention (e.g., compound of formula (I), (II), (III), (IV), (V), (VI), or (VII) or compound A or a salt (e.g., a pharmaceutically acceptable salt) thereof) can be isolated from human plasma.

In one embodiment, the present invention provides a method of preparing a compound represented by the following formula:

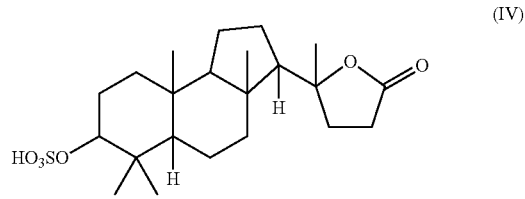

(IV)

or a salt thereof, comprising isolating the compound from human plasma.

In one embodiment, the present invention provides a method of preparing a compound represented by the following formula:

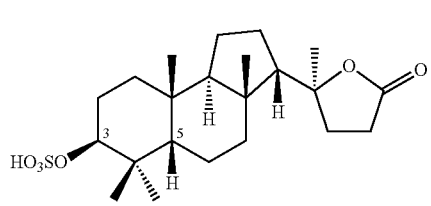

(VI)

or a salt thereof, comprising isolating the compound from human plasma.

The compound of formula (IV) or (VI) can be isolated from human plasma using various combinations of polar and nonpolar solvent because the compound is both anionic and lipophilic.

In one embodiment, the proteins in the human plasma is first precipitated with an organic solvent, such as methanol. The resulting suspension can then be centrifuged and the supernatant filtered. The resulting filtrate can then be acidified and passed over an anion exchange resin column. The anion exchange column can be rinsed with an acidic eluant, such as acidic methanol/water solution. The compound of formula (IV) or (VI) can then be eluted out from the column by using a basic organic solution, such as a basic methanol solution (e.g., methanol/NH$_4$OH solution). The eluate comprising the compound of formula (IV) or (VI) can then be collected and evaporated to dryness. The resulting salt/extract mixture can be suspended in an organic solvent, such as methanol. The salt can be removed from the suspension by filtration. The resulting filtrate can then be extracted with a nonpolar organic solvent, such as cyclohexane, to remove lipid components in the extract. The polar layer (or methanol layer) can be collected and evaporated to dryness. The resulting material can be suspended in an organic solvent, such as 1-butanol, and filtered. The resulting organic solution can be extracted with water to remove very polar compounds in the extract. The organic layer can then be evaporated to dryness and dissolved in water. The aqueous solution can be extracted with an organic solvent, such as ethyl acetate, to remove nonionic compounds with medium polarity. The water layer can then be collected and evaporated to dryness to provide crude product, which can be further purified using liquid chromatography. In one embodiment, the crude product is purified by silica column, more specifically a C18 reverse phase silica column.

In another embodiment, the present invention provides method of preparing a compound of formula (VII), a synthetic isomer of X12063 (i.e., compound of formula (VI)). The method comprises the steps of:

(1) isolating a compound of formula 3 from the resins of the evergreen *Ailanthus triphysa*

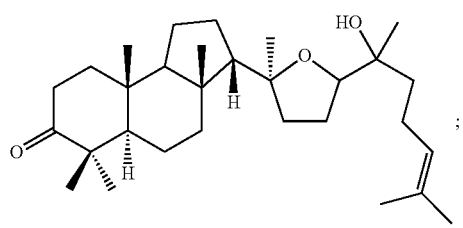

3

(2) reacting the compound of formula 3 with an oxidizing reagent to give a compound of formula 4:

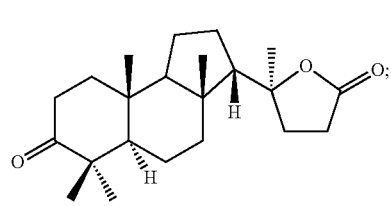

4

(3) reacting the compound of formula 4 with a reducing reagent to give a compound of formula 5:

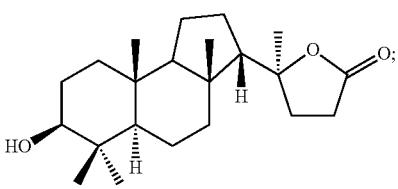

5

(4) reacting the compound of formula 5 with sulfuric acid to give the compound of formula (VII).

In one embodiment, the compound of formula 3 is isolated by extracting the resin of *Ailanthus triphysa* with an organic solvent, such as hexane.

Any suitable oxidation reagents can be used in step (2) of the method above. In one embodiment, the oxidizing reagent is pyridinium chlorochromate (PCC).

Any suitable reducing reagents can be used in step (3) of the method above. In one embodiment, the reducing reagents include, but are not limited to, LiAlH$_4$ and NaBH$_4$. In one embodiment, the reducing reagent is NaBH$_4$.

One route to obtain the isomer of X12063 that we have successfully followed is as follows:

Isolation of Malibaricol

Eight centrifuge tubes each containing *Ailanthus triphysa* extract (2.0 g, Halmaddi—India, Equinox Aromatics, LLC) and hexane (40 mL) were vortexed for 30 minutes and centrifuged for 5 minutes. The supernatant was transferred to a round-bottomed flask and the solvent removed under reduced pressure to give 11 g of the crude extract. The residue was purified by column chromatography on silica gel (60 Å, 230-400 mesh, gradient elution with 10-20% hexane/ethyl acetate) to give 2.3 g of Malibaricol (14% yield) as a light yellow oil.

Oxidation of Malibaricol

To a stirring solution of Malibaricol (2.43 g, 5.29 mmol, 1.0 eq) in DCM/HOAc (3:1, 100 mL) was added PCC (2.84 g, 13.2 mmol, 2.5 eq). The reaction mixture was stirred at 50° C. for 1 h and cooled to room temperature. The reaction mixture was stirred with silica gel (50 g) for 5 minutes and filtered through a pad of silica gel (DCM was used to completely wash the compound off of the silica). The solvent was removed under reduced pressure and the resultant oil was purified by column chromatography on silica gel (60 Å, 230-400 mesh, gradient elution with 10-50% hexane/ethyl acetate) to give 1.30 g of lactone (71% yield) as a light yellow oil.

Reduction of A-Ring Ketone

To a stirring solution of ketone (250 mg, 0.722 mmol, 1.0 eq) in THF/MeOH (1:2, 7.5 mL) at 0° C. was added NaBH$_4$ (32 mg, 0.867 mmol, 1.2 eq). The reaction mixture was stirred for 15 minutes and quenched by the addition of 10% H$_2$SO$_4$ (10 mL) and extracted with DCM. The combined organic extracts were dried over MgSO$_4$, filtered, concentrated under reduced pressure, and purified by column chromatography on silica gel (60 Å, 230-400 mesh, gradient elution with 10-50% hexane/ethyl acetate) to give 128 mg of alcohol (51% yield) as a light yellow oil.

Sulfation of Equatorial Alcohol

To a stirring solution of pyridine (1.25 mL) and H$_2$SO$_4$ (40 μL, 0.75 mmol, 3.0 eq) at room temperature was added Ac$_2$O (70 μL, 0.75 mmol, 3.0 eq). The mixture was stirred at 50° C. for 5 minutes and a solution of alcohol (87 mg, 0.25 mmol, 1.0 eq) in pyridine (0.5 mL) was added dropwise. After 20 min, the reaction mixture was cooled to room temperature and 25% NH$_4$OH (185 μL, ~0.8 eq NH$_3$) was added. After a sticky solid settled out in the bottom of the flask, the liquid was transferred to another flask and additional 25% NH$_4$OH (185 μL, ~0.8 eq NH$_3$) was added. The solvent was removed under reduced pressure and the residue dissolved in water (~1 mL) and purified by vacuum liquid chromatography (C18 Reversed Phase silica gel, elution with 20-50% MeOH/water). The fractions were concentrated under reduced pressure (at 50° C.) and held for about 6 h to give 63 mg of the ammonium sulfate salt (56%) as a white solid.

subjects in five categories of glycemic control. Category 1 subjects (642) had Normal fasting glucose/Normal glucose tolerance (NFG/NGT). Category 2 subjects (224) had Impaired fasting glucose/Normal glucose tolerance (IFG)/NGT. Category 3 subjects had Normal fasting glucose/Impaired glucose tolerance (NFG/IGT). Category 4 subjects (57) had Impaired fasting glucose/Impaired glucose tolerance (IFG/IGT). Category 5 subjects (12) had type 2 diabetes. The NFG/IFG status was determined based on the fasting plasma glucose test and the NGT/IGT status was determined using the Oral Glucose Tolerance Test (OGTT). The patients with diabetes didn't necessarily pass through the IFG or IGT categories. The X12063 (and other biomakers) were extracted from the plasma samples using methanol to produce an analytical sample and the levels in the analytical sample were determined using LC-MS/MS. The data show that the level of X12063 reflects the glycemic category of the subjects. The data for X12063 and another exemplary biomarker in these subjects is presented in FIG. 1.

The relative fasting plasma levels of X12063 increased in a cohort of healthy, non-diabetic subjects based on their glycemic status. The cohort consisted of 623 normal sub-

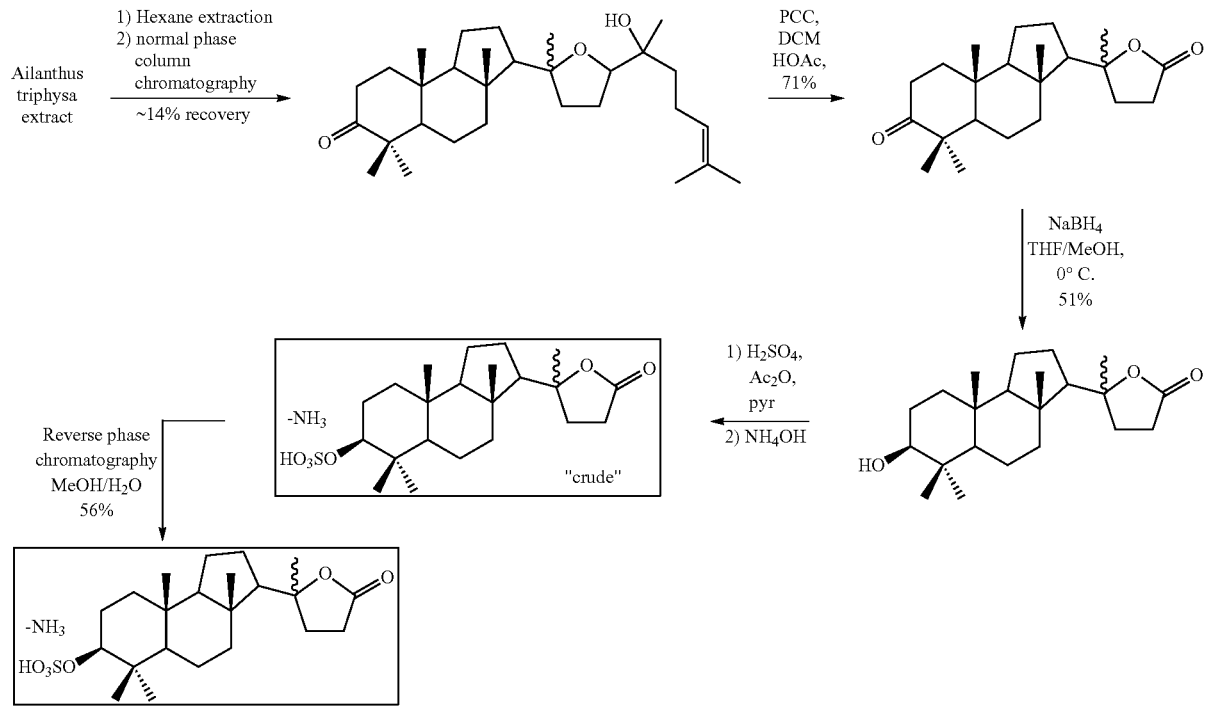

The leading references for the method are Chawla, A.; Dev, S. "A new class of triterpenoids from *Ailanthus Malabarica* DC derivatives of malabaricane," Tetrahedron Lett. 1967, (48), 4837-42 and Paton, William F.; Paul, Iain C.; Bajaj, Ashok G.; Dev, Sukh. "The structure of malabaricol," Tetrahedron Lett. 1979, (43), 4153-4.

EXAMPLES

Example 1. Metabolite Level is Significantly Elevated in Pre-Diabetic Subjects

The levels of X12063 (or compound A shown above) were measured by collecting fasting plasma samples from jects, 220 subjects with isolated impaired fasting glucose (iIFG), 56 subjects with isolated impaired glucose tolerance (iIGT) and 56 subjects with both impaired fasting glucose and impaired glucose tolerance. In the prediabetic states of isolated impaired fasting glucose (iIFG), isolated impaired glucose tolerance (iIGT), and combination IFG and IGT X12063 levels were significantly higher when compared to levels in normal subjects.

The results are presented in Table 1. In Table 1, the mean levels of X12063 are presented and the standard deviation is given in the parenthesis. The p-value was determined by the Wilcoxon test. FPG means fasting plasma glucose; 2hPG means the level of plasma glucose measured at 2 hour from the oral glucose tolerance test; normal means normal fasting plasma glucose; and normal glucose tolerance means FPG<100 & 2hPG<140 mg/dl; iIFG means isolated impaired fasting glucose where 100≤FPG<126 and 2hPG<140 mg/dl; iIGT means isolated impaired glucose tolerance where FPG<100 and 140≤2hPG<200 mg/dl; and combined IFG and IGT means 100≤FPG<126 and 140≤2hPG<200 mg/dl.

TABLE 1

| Variable | Normal | iIFG | iIGT | IFG & IGT |
|---|---|---|---|---|
| Number of subjects | 623 | 220 | 56 | 56 |
| X12063 (relative level) | 0.249 (0.18) | 0.308 (0.19) | 0.385 (0.27) | 0.407 (0.27) |
| p-value vs. normal | — | <.0001 | <.0001 | <.0001 |

In two independent studies, X12063 correlated ($r=0.35$, $r=0.32$) with the level of glucose measured at 2 h during an Oral Glucose Tolerance Test (OGTT). In these studies the level of the compound predicted the (classified the) subjects with impaired glucose tolerance (IGT) with an area under the receiver operator characteristic curve (AUC) of 0.68 and 0.70. The first study consisted of 517 subjects, 23% of whom were IGT and the second study consisted of 300 subjects, 21% of whom were IGT. In these studies, the AUC for fasting plasma glucose was 0.59 (Study 1) and 0.64 (Study 2).

Leave One Out Cross Validation (LOOCV) models were developed to predict the IGT subjects using combinations of measurements. The AUC for a model consisting of X12063+AHB+LGPC was 0.766 for the cohort in Study 1 and 0.797 for the cohort in Study 2. For the model consisting of X12063+AHB+LGPC+Serine+Isoleucine the AUC was 0.785 for the Study 1 cohort and 0.805 for the Study 2 cohort. Additional models, consisting of four to ten variables, were generated to predict IGT subjects in the study cohorts and the AUC was determined for each model. Several thousand models were generated, a portion of which had an AUC >0.78. Exemplary models having an AUC of at least 0.800 are presented in Table 2. The variable used in each model is indicated by an asterisk. Further models using seven variables were generated using LOOCV and the AUC was determined. Example seven variable models are presented in Table 3.

TABLE 2

Multi-variate models to predict IGT

| Variable | Number of Variables | | | | | | |
|---|---|---|---|---|---|---|---|
|  | 10 | 9 | 8 | 7 | 6 | 5 | 4 |
| Age | * | * | * |  |  |  |  |
| Creatine | * | * | * | * |  |  |  |
| Fasting Glucose | * | * | * | * | * | * | * |
| Glycine | * | * | * | * |  |  |  |
| Insulin | * | * |  |  | * |  |  |
| Linoleoyl-LPC (LGPC) | * | * | * | * | * | * | * |
| Oleic Acid | * | * | * | * | * |  |  |
| X12063 | * | * | * | * | * | * | * |
| 2-Hydroxybutyric Acid | * | * | * | * | * | * | * |
| 3-methyl-2-oxopentanoic Acid | * |  |  |  |  |  |  |
| AUC | 0.800 | 0.801 | 0.802 | 0.803 | 0.802 | 0.801 | 0.800 |

TABLE 3

Seven Variable Multi-variate Models to Predict IGT.

| Variable | | | | | | | | | |
|---|---|---|---|---|---|---|---|---|---|
| 2-Hydroxybutyric Acid | * | * | * | * | * | * | * | * | * |
| Fasting Glucose | * | * | * | * | * | * | * | * | * |
| Linoleoyl-LPC (LGPC) | * | * | * | * | * | * | * | * | * |
| X12063 | * | * | * | * | * | * | * | * | * |
| Oleic Acid | * | * |  | * | * | * | * | * | * |
| Glycine | * | * | * |  | * |  |  |  | * |
| Creatine | * |  | * | * |  |  | * |  |  |
| Age |  | * | * |  |  | * | * | * |  |
| 3-methyl-2-oxopentanoic Acid |  |  |  | * |  |  | * |  | * |
| Insulin |  |  |  |  |  | * | * |  |  |
| AUC | 0.803 | 0.802 | 0.801 | 0.801 | 0.801 | 0.800 | 0.800 | 0.800 | 0.800 |

Example 2. Monitoring Diet and Exercise Therapy in Subjects at Risk of Type 2 Diabetes X12063

170 subjects at risk for progression to type 2 diabetes (prediabetic IFG and/or IGT or having a diabetes risk score (FINDRISC) >12[#] underwent 12 weeks of lifestyle (diet and exercise) intervention. At baseline, this study was 49% female with a mean age of 54 and mean BMI of 30.9. Fasting plasma X12063 levels decreased significantly with the lifestyle intervention.

TABLE 4

12 week change summary

| Variable | % Decrease from baseline | P value vs. baseline |
|---|---|---|
| Weight | 4.1 | <.0001 |
| FPG | 3.0 | <.0001 |
| 2hPG | 4.8 | 0.03 |
| X12063 | 22.1 | <.0001 |

Example 3 Monitoring Diet, Exercise, and Metformin Therapy in IFG Subjects with X12063

33 subjects with IFG underwent a 12 week intervention including both lifestyle (diet and exercise) changes and drug (metformin, dose: 2 g/day) therapy. At baseline, this study was 49% female with a mean age of 54 and mean BMI of 30.9. Fasting plasma X12063 levels decreased significantly with the intervention.

TABLE 5

12 week change summary

| Variable | % Decrease from baseline | P value vs. baseline |
|---|---|---|
| Weight | 6.8 | <.0001 |
| FPG | 9.4 | <.008 |
| 2hPG | 13.0 | 0.02 |
| X12063 | 23.9 | <.0001 |

Example 4. Synthesis of 211-023 (Compound 2)

Compound 2 was synthesized in three steps from Malibaricol (compound 3), see Scheme 1.

Malibaricol (compound 3) is found in the resin of the evergreen *Ailanthus triphysa* (aka *Ailanthus malabarica*) which grows throughout India, Asia, and Australia. The hexane extract (Srinivas) of the resin was subjected to oxidative conditions (Chawla) resulting in cleavage of the side chain and formation of lactone (compound 4). Reduction of the ketone with NaBH$_4$ exclusively provided equatorial alcohol (compound 5). The alcohol was then reacted to form the sulfate under standard conditions, converted to the ammonium salt during workup, and isolated as ammonium salt (compound 2) using neutral reverse phase chromatography conditions detailed above.

Isolation of Malabaricol (Compound 3)

Eight 50 mL centrifuge tubes each containing *Ailanthus triphysa* extract (2.0 g, Halmaddi, India, Equinox Aromatics LLC) and hexane (40 mL) were vortexed for 30 minutes and centrifuged for 5 minutes. The supernatant was transferred to a round-bottomed flask and the solvent removed under reduced pressure to give 11 g of the crude extract. The residue was purified by column chromatography on silica gel (60 Å, 230-400 mesh, gradient elution with 10-20% hexane/ethyl acetate) to give 2.3 g of Malibaricol (compound 3) (14% yield) as a light yellow oil.

Malabaricol Lactone (Compound 4)

To a stirring solution of Malabaricol (2.43 g, 5.29 mmol, 1.0 eq.) in DCM/HOAc (3:1, 100 mL) was added PCC (2.84 g, 13.2 mmol, 2.5 eq.). The reaction mixture was stirred at 50° C. for 1 h and cooled to room temperature. The reaction mixture was stirred with silica gel (50 g) for 5 minutes and filtered through a pad of silica gel (DCM was used to completely wash the compound off of the silica). The solvent was removed under reduced pressure and the resultant oil was purified by column chromatography on silica gel (60 Å, 230-400 mesh, gradient elution with 10-50% hexane/ethyl acetate) to give 1.30 g of lactone 4 (71% yield) as a light yellow oil. $^1$H NMR were recorded on a 300-MHz

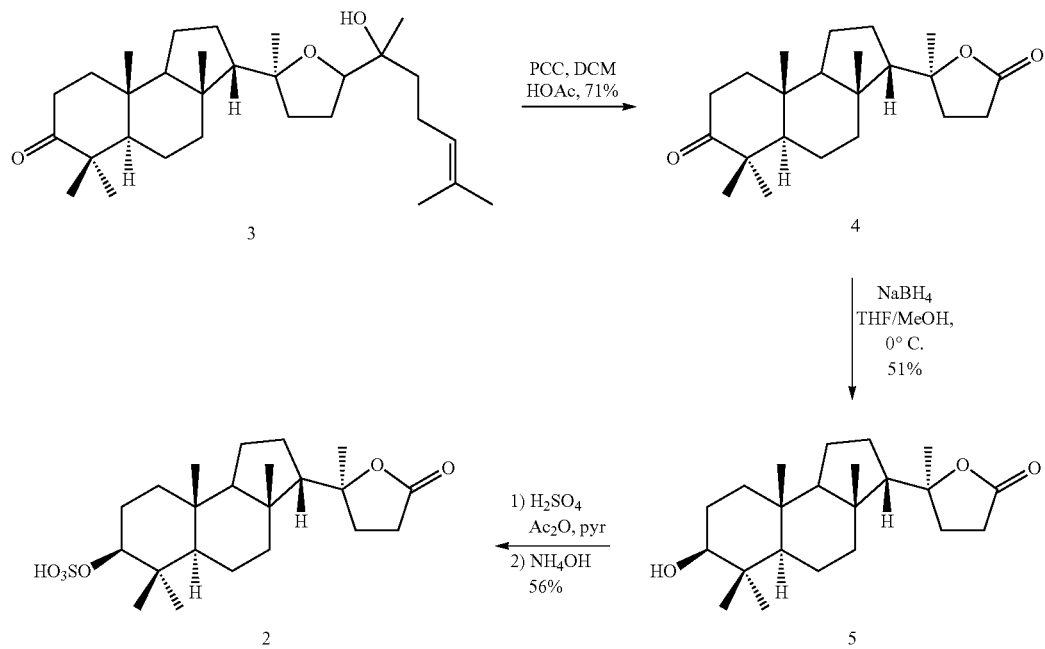

Scheme 1

Varian Inova and taken in $CDCl_3$. Mass spectra were recorded on a Thermo Scientific Orbitrap Elite Hybrid Ion Trap-Orbitrap Mass Spectrometer. $^1$H NMR (400 MHz, CDCl3) δ 2.50-2.65 (m, 3H), 2.41 (ddd, J=16.4, J=7.5, J=3.6), 2.1-2.3 (m, 1H), 2.9-2.1 (m, 3H), 1.7-1.9 (m, 3H), 1.5-1.7 (m, 8H), 1.42 (s, 3H), 1.3-1.4 (m, 2H), 1.11 (s, 3H), 1.06 (s, 3H), 1.04 (s, 3H), 0.99 (s, 3H); HRMS (ESI+): m/z calculated for $C_{22}H_{37}NO_3$ (M+H+NH$_3$), 364.2846, found: 364.2846.

Sulfated Alcohol of Malibaricol Lactone (Compound 2)

To a stirring solution of ketone (250 mg, 0.722 mmol, 1.0 eq.) in THF/MeOH (1:2, 7.5 mL) at 0 °C. was added $NaBH_4$ (32 mg, 0.867 mmol, 1.2 eq.). The reaction mixture was stirred for 15 minutes and quenched by the addition of 10% $H_2SO_4$ (10 mL) and extracted several times with DCM. The combined organic extracts were dried over $MgSO_4$, filtered, concentrated under reduced pressure, and purified by column chromatography on silica gel (60 Å, 230-400 mesh, gradient elution with 10-50% hexane/ethyl acetate) to give 128 mg of alcohol 5 (51% yield) as a light yellow oil. The alcohol (87 mg, 0.25 mmol, 1.0 eq) was then prepared as a solution in pyridine (0.5 mL). Separately, $Ac_2O$ (70 μL, 0.75 mmol, 3.0 eq.) was added to a stirring solution of pyridine (1.25 mL) and $H_2SO_4$ (40 μL, 0.75 mmol, 3.0 eq.) at room temperature. The mixture was stirred at 50° C. for 5 minutes and the alcohol/pyridine solution was added drop wise. After 20 min, the reaction mixture was cooled to room temperature and 25% $NH_4OH$ (185 μL, ~0.8 eq. NH3) was added. After a sticky solid settled out in the bottom of the flask, the supernatant was transferred to another flask and additional 25% $NH_4OH$ (185 μL, ~0.8 eq. NH3) was added. The solvent was removed under reduced pressure and the residue dissolved in water (~1 mL) and purified by vacuum liquid chromatography (C18 Reversed Phase silica gel, elution with 20-50% MeOH/water). The pure fractions were concentrated under reduced pressure (at ~50° C.) and held for about 6 h to give 63 mg of ammonium sulfate salt (2) (56%) as a white solid.

Example 5. Isolation, Purification and Structure Elucidation of X12063

1. General Materials

Plasma samples were purchased from Bioreclamation, LLC. (Westbury, N.Y.). Authentic standards of d7-glucose, d3-leucine, d8-phenylalanine, d6-cholesterol, d3-methionine, d15-octanoic acid and d5-tryptophan were purchased from Cambridge Isotope Laboratories (Andover, Mass.). D19-decanoic acid, d27-tetradecanoic acid, d35-octadecanoic acid and d2-eicosanoic acid were procured from C/D/N Isotopes, Inc. (Pointe-Claire, Quebec). Bromophenylalanine, DL-4-chlorophenylalanine, DL-2-fluorophenylglycine and tridecanoic acid were provided by Sigma-Aldrich Co. LLC. (St. Louis, Mo.). Analytical and semi-preparative C18 columns were purchased from Waters (Milford, Mass.). Normal phase, chiral columns were purchased from Chiral Technologies Inc. (West Chester, Pa.). Anion exchange resin columns and resin (for larger scale solid phase extraction) was purchased from Sigma-Aldrich (St. Louis, Mo., USA).

a) Extraction of X12063

Due to the low abundance of X12063 in plasma, it was estimated that 40 L of plasma would need to be extracted to obtain sufficient material for NMR analysis. Each step of the extraction was monitored by LC-MS and optimized for extraction efficiency. For the extraction, we took advantage of X12063's dual physicochemical nature, its anionic and lipophilic properties and were able to extract by using various combinations of polar and nonpolar solvent partitioning.

A total of 40 L of human citrate plasma was processed in 1 L portions. Plasma was subjected to protein precipitation by vigorously mixing 1 L of plasma with 3 L of methanol. The resulting suspension was centrifuged. The supernatant was filtered, and subsequently diluted with an equal amount of deionized water to yield approximately 7 L of extract per 1 L of plasma. 7 L of extract were acidified with 12N HCl (20 mL per 1 L of extract) and passed over an anion exchange resin column (300 g of Amberlite IRA 96, 3" ID column) that was rinsed with 2 L of deionized water and equilibrated with 1 L of 0.1 N HCl in water, prior to loading. After loading the extract, the resin was rinsed with 1 L of 0.1 N HCL in methanol/water (1:3) and subsequently eluted with 1 L of 4% NH4OH in methanol. The first 300 mL of near colorless eluate were discarded. The following 700 mL of eluate (yellow colored) were collected and evaporated to near dryness. Ammonium chloride precipitated during evaporation. The extract/salt mixture was suspended 5× sequentially in 50 mL portions of methanol and filtered. The resulting methanolic solution was extracted with 250 mL cyclohexane (to remove lipids). The methanol layer was evaporated to near dryness. Again, a precipitate of ammonium chloride salt was formed. The extract/salt mixture was suspended 5× sequentially in 50 mL portions of 1-butanol and filtered. The 1-butanol phase was extracted with 250 mL of water (removal of very polar compounds). The 1-butanol layer was evaporated to dryness and dissolved in 200 mL of water and extracted with 250 mL of ethyl acetate (removal of nonionic compounds of medium polarity). The water layer was evaporated to dryness and dissolved by sequentially adding 2 mL of methanol and 1 mL of water and was further diluted with an equal volume of water.

Extracts from 5 L lots of plasma were combined and subjected to C18 reversed phase vacuum liquid chromatography. Extract was loaded onto a 60 mL polypropylene column with 10 g of C18 reversed phase silica gel (VersaFlash C18, 45-75 m, Supelco) that was activated with 30 mL of methanol and subsequently rinsed with 30 mL of water, prior to loading with extract. The column was eluted under vacuum with a methanol/water step gradient. Fractions of 10-15 mL were collected and tested by LC-MS. X12063 containing fractions (50 to 60% methanol) were combined and evaporated to dryness.

b) Purification

Dried VLC X12063 fractions from extraction of one 5 L lot of plasma were dissolved in methanol/water (1:3) and chromatographed on a BEH C18 reversed phase column (XBridge BEH C 18, 2.5 μm, 4.6×150 mm, Waters) using a shallow gradient; 45% B to 65% B in 7 minutes, 65% B to 98% B in 2 minutes (to wash column); mobile phase A: 6.5 mM ammonium bicarbonate in water; mobile phase B: 6.5 mM ammonium bicarbonate in water/methanol (1:19) using mass spectrometric detection (Thermo Quantum Ultra with HESI source; negative ion mode). Collection of the X12063 fraction was carried out by time utilizing the divert valve on the Thermo Quantum mass spectrometer. Analysis of the X12063 fraction demonstrated that X12063 had been enriched in the fraction which also contained androsterone sulfate.

The X12063 fraction was evaporated to dryness and once again dissolved in methanol/water (1:3) for secondary purification, this time using a chiral OJ-3R column (2.5 μm, 2.1×100 mm, Chiral Technologies) and an isocratic gradient; 45% B for 7 minutes; mobile phase A: 6.5 mM ammonium bicarbonate in water; mobile phase B: 6.5 mM ammonium bicarbonate in water/methanol (1:19) using mass spectrometric detection (Thermo Quantum Ultra with HESI source; negative ion mode). Collection of the X12063 fraction was carried out by time utilizing the divert valve on the Thermo Quantum mass spectrometer. Analysis of the X12063 fraction demonstrated that X12063 had been purified.

The extracts from the remaining 5 L plasma lots were combined and purified by Scynexis Inc. (Durham, N.C.) via LC-MS purification using an XBridge C18 reversed phase column (5 µm, 10×150 mm, Waters Corp.) an a gradient; 50% B for 12 minutes, 50% B to 80% B in 3 minutes, 80% B for 0.6 minutes to wash column; mobile phase A: 8.2 mM ammonium bicarbonate in water; mobile phase B: 8.2 mM ammonium bicarbonate in water/methanol (5:95). X12063 fractions were collected by mass directed purification. Following this large scale purification, the X12063 fraction was evaporated to dryness, reconstituted in methanol/water (1:3) and secondary purification was carried out using the chiral OJ-3R column as above.

Once LC-MS analysis of all of the X12063 fractions had confirmed the purity of each fraction, fractions were combined and evaporated to dryness to allow for LC-MS/MS" and NMR analysis of the purified compound for structure elucidation.

c) Metabolomic Profiling and Structure Elucidation LC-MS/MS Analysis

Plasma samples for LC-MS/MS analysis were stored at −80° C. until needed and then thawed on ice just prior to extraction. Extraction of samples for LC-MS/MS analysis was executed using an automated liquid handling robot (Hamilton LabStar, Hamilton Robotics, Inc., Reno, Nev.), where 450 µL of methanol was added to 100 µl of sample to precipitate proteins. The methanol contained four recovery standards, DL-2-fluorophenylglycine, tridecanoic acid, d6-cholesterol and 4-chlorophenylalanine to allow confirmation of extraction efficiency. An aliquot of each sample was taken from the extract and dried. The samples were then reconstituted in 50 µL of 6.5 mM ammonium bicarbonate in water (pH 8) for the negative ion analysis. Reconstitution solvents contained instrument internal standards (as listed in above in General Materials) to assess instrument performance and to serve as retention index markers for chromatographic alignment.

LC separations of both the whole plasma extract and the purified extract from citrate plasma were performed using a Waters Acquity UPLC (Waters, Milford, Mass.). Reverse-phase negative ion analysis used mobile phase consisting of 6.5 mM ammonium bicarbonate in water, pH 8 (A) and 6.5 mM ammonium bicarbonate in 95% methanol/5% water (B). The gradient was run at 0.35 ml/min with the profile of 0.5% B to 70% B in 4 minutes, followed by a 0.5 minute ramp to 98% B, hold at 98% B for 0.9 minutes, then 0.2 minutes back to 0.5% B, and finally a 5.4 minute equilibration at 0.5% B, for a total run time of 11 minutes. The sample injection volume was 5 µL and a 2× needle loop overfill was used. Separations utilized a 2.1 mm×100 mm Waters BEH C18 1.7 µm columns held at 40° C.

Primarily, a ThermoFisher Scientific (Waltham, Mass.) Orbitrap Elite was utilized for structural characterization analyses given its ability to perform directed rounds of fragmentation. A Q-Exactive (ThermoFisher) was also used to generate a quadrupole based fragmentation spectrum that was not subject to the ⅓ mass cutoff rule. For structure elucidation, the peak of interest was subjected to multiple rounds of fragmentation, such that a detailed accurate mass fragmentation tree was generated. Mass calibration was performed as needed to maintain <5 ppm mass error for all standards monitored.

d) NMR Analysis

The NMR solutions of X12063 and 211-023 (see Example 4 above) were prepared by dissolving the available purified material in 200 µL aliquots of $d_6$-DMSO. The estimated quantities were ~25-50 µg for X12063 and ~3-5 mg for 211-023. The solutions were transferred to 3 mm NMR tubes and 20 µl aliquots of D20 were added to each tube to remove exchangeable protons.

NMR data were recorded at 25° C. using an Agilent DD2 800 MHz NMR spectrometer equipped with a triple resonance cold probe and a cold carbon preamp. $^1$H spectra were obtained with PURGE (Simpson) presaturation of the water and residual DMSO peaks, a spectral width (SW) of 8 kHz, a 3.8 s acquisition time (AT), 2 second presaturation delay and digitized using 32 k point. zTOCSY (Trippleton) and NOESY (Macura) data were recorded with 8 kHz SW and 2K points The homonuclear 2D sequences were the standard sequences from Agilent and were used with PURGE (Simpson) presaturation of the water and residual DMSO peaks. TOCSY data were collected in the phase-sensitive mode using the hypercomplex method with 128 increments, 40 scans per increment for X12063 and 4 scans for 211-023, and mixing times of 30 and 100 ms in TOCSY and 500 ms in NOESY. NOESY data were also collected in the phase-sensitive mode using the hypercomplex method, but with 200 increments and 48 scans per increment. The final 2D matrices were 2K×2K with Gaussian weighting in both dimensions.

Single bond $^1$H, $^{13}$C 2D chemical shift correlation spectra were recorded in inverse mode using $^1$H detection using a sensitivity-enhanced HSQC sequence with $^{13}$C decoupling, bip or adiabatic 180° pulses for both channels, and multiplicity editing. (Boyer, Hu) Two sets of 128 time increments were obtained in the hypercomplex phase-sensitive mode with 2K points in t2. 320 scans were recorded per time increment, and the 2D data were processed using Gaussian functions and zero-filled to a final size of 2K×2K.

Proton-detected multiple bond 2D correlation spectra (HMBC)(Bax) were recorded in the hypercomplex phase-sensitive mode without 13C decoupling during acquisition. The HMBC spectra were plotted in a mixed mode [absolute value in f2 ($^1$H) and phase-sensitive in f1 ($^{13}$C)]. A shifted Gaussian weighting function was used along f2 and a cosine weighting function was used along f1. Two sets of 120 time increments were recorded with 2K points in t2, and zero-filled to a final size of 2K×2K. The filter delay corresponded to an average $^1J_{C,H}$ of 140 Hz, and 600 transients were obtained per increment for X12063 and 64 for 211-023. The long range 1H-$^{13}$C couplings were allowed to evolve for a delay of 83 ms (6 Hz optimization).

$^1$H-decoupled $^{13}$C spectra was recorded for 211-023 only with a 48076.92 Hz SW using a carbon echo-type pulse sequence (Smith) to minimize probe ring down.

2. LC-MS/MS and NMR Analysis

LC-MS/MS and NMR analysis of the extract, and comparison of the resulting data to that acquired on the synthetically derived stereoisomer (211-023, see Example 4) of X12063 have allowed the elucidation of the structure and stereochemistry of X12063 as shown in formula (VI).

Example 6. X12063 as a Biomarker of Glucose Tolerance

X12063 levels were measured in 3 sets of subjects in fasting plasma samples taken at time=0 during an oral glucose tolerance test (OGTT). The subjects came from the Relationship between Insulin Sensitivity and Cardiovascular disease (RISC) study 3 year follow up and two subcohorts of the Diabetes Mellitus and Vascular Health Initiative (DMVhi) study. These latter two groups were composed of subjects at risk for progression to diabetes by virtue of a FINDRISC score, a non-clinical risk assessment test, of >12 and/or having impaired glucose tolerance (IGT) and/or impaired fasting glucose (IFG). The first is an observational cohort which is part of the DEXLIFE (Diet and Exercise for Life) program (DEXLIFE DMVhi, n=668) and the second is a diet and exercise intervention study (DEXLIFE Lifestyle Intervention (DLI) n=170).

X12063 levels were found to be highly correlated with several anthropometric and metabolic parameters in all 3 groups of study subjects (Table 6). In particular, X12063 levels are most strongly correlated with BMI and body weight, and, to a lesser degree, plasma insulin. In the RISC study, X12063 levels were significantly elevated versus normal in type 2 diabetes and in 3 distinct, non-overlapping prediabetic states: isolated IFG, isolated IGT, and combination IFG and IGT (Table 7). The associations with these three prediabetic states were further analyzed by computing odds ratios versus normal for each state for a one standard deviation change in X12063 level while also including a correction for age, sex, and BMI. By this analysis, X12063 was significantly associated with the two IGT states, isolated IGT and combination IFG and IGT, but not with isolated IFG.

In the DLI study, body weight, FPG, and 2hPG were all significantly reduced after the 12 week intervention. This was accompanied by significant reductions in X12063 levels. The control group had no significant changes in body weight, FPG, 2hPG, or X12063. Changes in X12063 during the intervention correlated with changes in several efficacy parameters. Most notable were the correlations for change in body weight (r=0.50) and BMI (r=0.49).

TABLE 6

Pearson Correlations with X12063 plasma levels

|  | RISC | DEXLIFE DMVhi | DLI baseline |
|---|---|---|---|
| n | 955 | 668 | 170 |
| BMI | 0.42 | 0.37 | 0.44 |
| Body Weight | 0.41 | 0.35 | 0.44 |
| Insulin | 0.35 | 0.37 | 0.29 |
| FPG | 0.18 | 0.25 | 0.21 |
| 2hPG | 0.22 | 0.15 | 0.13* |

All p values < .05 except *

TABLE 7

X12063 Levels in RISC by Glycemic Category

| Normal | Isolate IGT | Isolated IFG | IGT & IFG | T2D |
|---|---|---|---|---|
| 623 | 56 | 220 | 56 | 10 |
| 0.249 ± 0.18 | 0.385 ± 0.28† | 0.308 ± 0.19† | 0.407 ± 0.27† | 0.367 ± 0.20‡ |

All values = area ratio;
mean ± SD;
vs normal: †p < 0.0001 by the Wilcoxon test

The present invention also provides the following embodiments:

Embodiment 1

A method for diagnosing a disease or disorder selected from the group consisting of insulin resistance, a metabolic disorder, diabetes and pre-diabetes in a subject comprising:

(1) determining the level of a compound represented by formula (I):

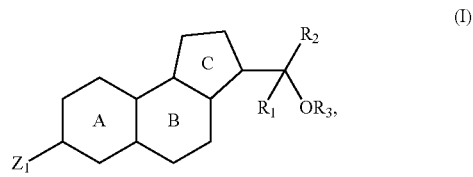

or a salt thereof wherein:

Rings A, B and C are optionally substituted with one or more substituents selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl;

Z$_1$ is —OH, —OR$^a$, —OSO$_3$H, —OPO(OH)$_2$, —OC(=O)R$^b$, —OC(=O)NR$^c$R$^d$ or =O;

R$_1$ is a (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

R$_2$ is H, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

R$_3$ is H, —C(=O)R$^b$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkynyl;

or OR$_3$ together with R$_2$ forms a 3 to 9 membered ring optionally substituted with =O, (C$_1$-C$_6$)alkyl, —OH or —OR$^a$;

R$^a$ is (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R^b$ is H or a ($C_1$-$C_6$)alkyl;

$R^c$ and $R^d$ are each independently H or a ($C_1$-$C_6$)alkyl; and $R^e$, $R^f$, $R^g$ and $R^h$ are each independently H or a ($C_1$-$C_6$)alkyl;

wherein each of ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, halo($C_1$-$C_6$)alkyl and hydroxyl($C_1$-$C_6$)alkyl in a biological sample from the subject; and (2) comparing the level of the compound in the biological sample with the level of the compound in a normal control sample, wherein an altered level of the compound in the biological sample is indicative of the disease or disorder in the subject.

Embodiment 2

The method of Embodiment 1, wherein the method further comprises treating the subject with an effective therapy suitable for treating the disease or disorder when an altered level of the compound is present in the biological sample as compared to the level of the compound in the normal control sample.

Embodiment 3

A method for monitoring the progression or regression of a disease or disorder selected from the group consisting of insulin resistance, a metabolic disorder, diabetes and pre-diabetes in a subject comprising:

(1) determining the level of a compound represented by formula (I):

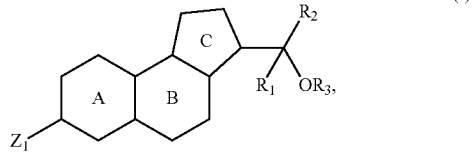

(I)

or a salt thereof wherein:

Rings A, B and C are optionally substituted with one or more substituents selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl;

$Z_1$ is —OH, —$OR^a$, —$OSO_3H$, —OPO(OH)$_2$, —OC(=O)$R^b$, —OC(=O)$NR^cR^d$ or =O;

$R_1$ is a ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R_2$ is H, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R_3$ is H, —C(=O)$R^b$, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

or $OR_3$ together with $R_2$ forms a 3 to 9 membered ring optionally substituted with =O, ($C_1$-$C_6$)alkyl, —OH or —$OR^a$;

$R^a$ is ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R^b$ is H or a ($C_1$-$C_6$)alkyl;

$R^c$ and $R^d$ are each independently H or a ($C_1$-$C_6$)alkyl; and $R^e$, $R^f$, $R^g$ and $R^h$ are each independently H or a ($C_1$-$C_6$)alkyl;

wherein each of ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, halo($C_1$-$C_6$)alkyl and hydroxyl($C_1$-$C_6$)alkyl, in a first biological sample obtained at a first time from the subject;

(2) determining the level of the compound in a second biological sample obtained from the subject at a second time, wherein the second time is later than the first time; and (3) comparing the level of the compound in the second biological sample with the level of the compound in the first biological sample, wherein a change in the level of the compound is indicative of progression or regression of the disease in the subject.

Embodiment 4

The method of Embodiment 3, wherein the method further comprises treating the subject with an effective therapy suitable for treating the disease or disorder when regression of the disease or disorder is observed.

Embodiment 5

A method of monitoring the efficacy of insulin resistance treatment, a metabolic disorder treatment, diabetes treatment or pre-diabetes treatment in a subject, the method comprising the steps of:

(1) determining the level of a compound of formula (I):

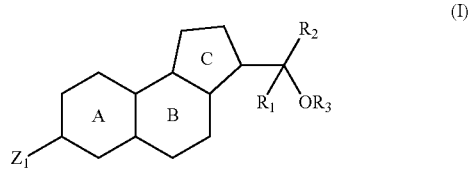

(I)

or a salt thereof, wherein:

Rings A, B and C are optionally substituted with one or more substituents selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl;

$Z_1$ is —OH, —$OR^a$, —$OSO_3H$, —OPO(OH)$_2$, —OC(=O)$R^b$, —OC(=O)$NR^cR^d$ or =O;

$R_1$ is a ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R_2$ is H, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R_3$ is H, —C(=O)$R^b$, ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

or $OR_3$ together with $R_2$ forms a 3 to 9 membered ring optionally substituted with =O, ($C_1$-$C_6$)alkyl, —OH or —$OR^a$;

$R^a$ is ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, heteroaryl($C_2$-$C_6$)alkynyl;

$R^b$ is H or a ($C_1$-$C_6$)alkyl;

$R^c$ and $R^d$ are each independently H or a ($C_1$-$C_6$)alkyl; and $R^e$, $R^f$, $R^g$ and $R^h$ are each independently H or a ($C_1$-$C_6$)alkyl;

wherein each of ($C_1$-$C_6$)alkyl, ($C_2$-$C_6$) alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^hC$(=O)$R^e$, —$NR^hC$(=O)$OR^e$, ($C_1$-$C_6$)alkyl, halo($C_1$-$C_6$)alkyl and hydroxyl($C_1$-$C_6$)alkyl, in a biological sample from the subject;

(2) treating the subject with a effective therapy for insulin resistance, a metabolic disorder, diabetes or pre-diabetes;

(3) analyzing a second biological sample from the subject to determine the level of the compound of formula (I), wherein the second sample obtained from the subject at a second time point after treatment; and (4) comparing the level of the compound of formula (I) in the first sample to the level of the compound of formula (I) in the second sample to assess the efficacy of the treatment for treating insulin resistance, a metabolic disorder, diabetes or pre-diabetes.

Embodiment 6

The method of any one Embodiments 2, 4 and 5, wherein the treating the subject comprising administering to the subject an effective amount of a therapeutic agent suitable for treating the disease or disorder.

Embodiment 7

The method of Embodiment 6, wherein the therapeutic agent is an antidiabetic or antiobesity drug.

Embodiment 8

The method of Embodiment 6, wherein the therapeutic agent is selected from the group comprising metformin, pioglitazone, rosiglitazone, acarbose, tetrahydrolipstatin, and phentermine/topiramate.

Embodiment 9

The method of any one of Embodiments 2, 4 and 5, wherein treating the subject comprises a lifestyle modification of the subject.

Embodiment 10

The method of Embodiment 9, wherein the lifestyle modification comprises modification and/or an increase in activity or exercise Embodiment 11. The method of any one of Embodiments 1 to 10, wherein the level of the compound is determined by chromatography, mass spectrometry, ELISA, antibody linkage or enzymatic reactions or assays.

Embodiment 12

The method of Embodiment 11, wherein the level of the compound is determined by tandem liquid chromatography-mass spectrometry (LC-MS/MS).

Embodiment 13

The method of any one of Embodiments 1 to 12, wherein the method further comprises analyzing the biological sample to determine the level of one or more additional biomarkers, wherein the additional biomarkers are related to the disease or disorder.

Embodiment 14

The method of Embodiment 13, wherein the one or more additional biomarkers are selected from the group consisting of 2-hydroxybutyrate (AHB), linoleoyl lysophosphatidylcholine (LGPC), oleate, 4-methyl-2-oxo-pentanoate, panthothenate (vitamin B5), beta-hydroxybutyrate (BHBA), and serine.

Embodiment 15

The method of Embodiment 14, wherein the method further comprises analyzing the biological sample to determine the level of 2-hydroxybutyrate (AHB) and linoleoyl lysophosphatidylcholine (LGPC), Embodiment 16. The method of any one of Embodiments 13 to 15, wherein the method further comprises analyzing the biological sample to determine the level of one or more additional biomarkers selected from the group consisting 3-methyl-2-oxo-butyric acid, alpha-ketoglutarate, creatine, glycine, isoleucine, leucine, leucine, oleoyl lysophosphatidylcholine, phenylalanine, trigonelline, tyrosine, valine, hydrocinnamic acid, xanthine, mannose, 3-methyl-2-oxovalerate, glycerolphosphorylcholine, adrenate, 3-methyl-2-oxo-pentanoate, 2-methylsuccinate, 1-octadecanol, 2-aminoadipate, 3-hydroxyisobutyrate, alpha-tocopherol, arginine, betaine, decanoylcarnitine, docosatetraenoic acid, glutamic acid, linoleic acid, linolenic acid, margaric acid, N-acetylglycine, octanoylcarnitine, palmitate, palmitoleic acid, palmitoyl lysophosphatidylcholine, stearate, threonine, and tryptophan.

Embodiment 17

The method of any one of Embodiments 13 to 16, wherein the method further comprises analyzing the biological sample to determine the fasting glucose level.

Embodiment 18

The method of any one of Embodiments 1 to 17, wherein the compound is represented by structural formula (II):

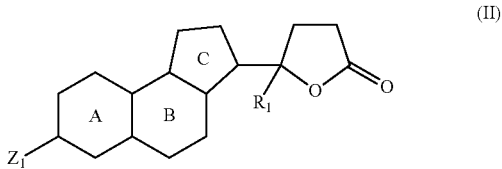

(II)

or a salt thereof, wherein $Z_1$ is —$OR^a$, —$OSO_3H$, —$OPO(OH)_2$, —$OC(=O)R^b$, or —$OC(=O)NR^cR^d$.

Embodiment 19

The method of Embodiment 18, wherein the compound is represented by structural formula (III):

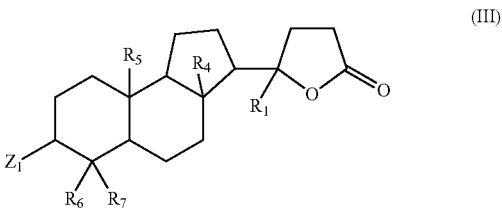

(III)

or a salt thereof, wherein:

$R_4$, $R_5$, $R_6$ and $R_7$ are each independently selected from the group consisting of —H, halogen, —CN, —$NO_2$, —$OR^e$, —$SR^e$, —$NR^fR^g$, —$C(=O)OR^e$, —$OC(=O)R^e$, —$C(=O)R^e$, —$C(=O)NR^fR^g$, —$OC(=O)NR^fR^g$, —$NR^hC(=O)R^e$, —$NR^hC(=O)OR^e$, ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl;

wherein each of ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —$C(=O)OR^e$, —$OC(=O)R^e$, —$C(=O)R^e$, —$C(=O)NR^fR^g$, —$OC(=O)$ $NR^fR^g$, $-NR^hC(=O)R^e$, $-NR^hC(=O)OR^e$, $(C_1-C_6)$alkyl, halo$(C_1-C_6)$alkyl and hydroxyl$(C_1-C_6)$alkyl.

Embodiment 20

The method of Embodiment 18 or 19, wherein $R_1$ is a $(C_1-C_6)$alkyl.

Embodiment 21

The method of Embodiment 20, wherein $R_1$ is methyl.

Embodiment 22

The method of any one of Embodiments 19 to 21, wherein $R_4$, $R_5$, $R_6$ and $R_7$ are each independently —H, halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, $(C_1-C_6)$alkyl, halo$(C_1-C_6)$alkyl and $(C_1-C_3)$alkoxy$(C_1-C_6)$alkyl.

Embodiment 23

The method of Embodiment 22, wherein $R_4$, $R_5$, $R_6$ and $R_7$ are each independently $(C_1-C_6)$alkyl or halo$(C_1-C_6)$alkyl.

Embodiment 24

The method of Embodiment 23, wherein $R_4$, $R_5$, $R_6$ and $R_7$ are all methyl.

Embodiment 25

The method of any one of Embodiments 1 to 17, wherein the compound is represented by the structural formula (IV):

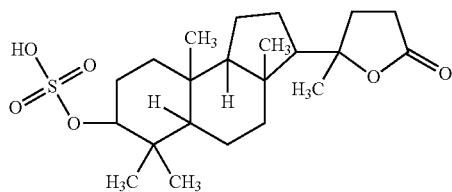

or a salt thereof.

Embodiment 26

The method of any one of Embodiments 1 to 17, wherein the compound is:

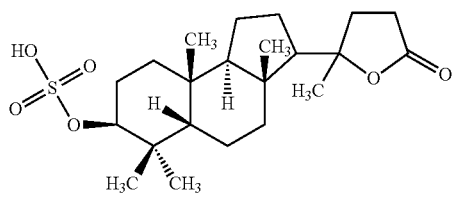

or a salt thereof.

Embodiment 27

The method of Embodiment 26, wherein the compound is at least 60% optically pure.

Embodiment 28

The method of Embodiment 26, wherein the compound is at least 70% optically pure.

Embodiment 29

The method of Embodiment 26, wherein the compound is at least 80% optically pure.

Embodiment 30

The method of Embodiment 26, wherein the compound is at least 90% optically pure.

Embodiment 31

The method of Embodiment 26, wherein the compound is at least 95% optically pure.

Embodiment 32

The method of Embodiment 26, wherein the compound is at least 99% optically pure.

Embodiment 33

The method of any one of Embodiments 1 to 32, wherein the compound is substantially free of impurities.

Embodiment 34

The method of Embodiment 33, wherein the compound is at least 60% pure.

Embodiment 35

The method of Embodiment 33, wherein the compound is at least 70% pure.

Embodiment 36

The method of Embodiment 33, wherein the compound is at least 80% pure.

Embodiment 37

The method of Embodiment 33, wherein the compound is at least 90% pure.

Embodiment 38

The method of Embodiment 33, wherein the compound is at least 95% pure.

Embodiment 39

The method of Embodiment 33, wherein the compound is at least 99% pure.

Embodiment 40

A kit comprising a compound represented by formula (I):

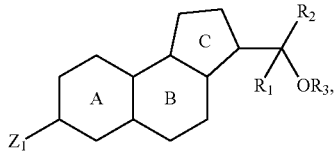

(I)

or a salt thereof, wherein:

Rings A, B and C are optionally substituted with one or more substituents selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl;

$Z_1$ is —OH, —OR$^a$, —OSO$_3$H, —OPO(OH)$_2$, —OC(=O)R$^b$, —OC(=O)NR$^c$R$^d$ or =O;

$R_1$ is a (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

$R_2$ is H, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

$R_3$ is H, —C(=O)R$^b$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

or OR$_3$ together with R$_2$ forms a 3 to 9 membered ring optionally substituted with =O, (C$_1$-C$_6$)alkyl, —OH or —OR$^a$;

R$^a$ is (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl (C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

R$^b$ is H or a (C$_1$-C$_6$)alkyl;

R$^c$ and R$^d$ are each independently H or a (C$_1$-C$_6$)alkyl; and

R$^e$, R$^f$, R$^g$ and R$^h$ are each independently H or a (C$_1$-C$_6$)alkyl;

wherein each of (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl groups described above is optionally substituted with 1 to 5 substituents independently selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, halo(C$_1$-C$_6$)alkyl and hydroxyl(C$_1$-C$_6$)alkyl; and instructions for diagnosing and monitoring a disease or disorder selected from the group consisting of insulin resistance, a metabolic disorder, diabetes and pre-diabetes in a subject based on the level of the compound detected in a biological sample from the subject.

Embodiment 41

The kit of Embodiment 40, wherein the kit comprises one or more additional biomarkers, wherein the additional biomarkers are related to the disease or disorder.

Embodiment 42

The kit of Embodiment 41, wherein the one or more additional biomarkers are selected from the group consisting of 2-hydroxybutyrate (AHB), linoleoyl lysophosphatidylcholine (LGPC), oleate, 4-methyl-2-oxo-pentanoate, panthothenate (vitamin B5), beta-hydroxybutyrate (BHBA), and serine.

Embodiment 43

The method of Embodiment 42, wherein kit further comprises 2-hydroxybutyrate (AHB) and linoleoyl lysophosphatidylcholine (LGPC) as the additional biomarkers,

Embodiment 44

The kit of any one of Embodiments 41 to 43, wherein the kit further comprises one or more additional biomarkers selected from the group consisting 3-methyl-2-oxo-butyric acid, alpha-ketoglutarate, creatine, glycine, isoleucine, leucine, leucine, oleoyl lysophosphatidylcholine, phenylalanine, trigonelline, tyrosine, valine, hydrocinnamic acid, xanthine, mannose, 3-methyl-2-oxovalerate, glycerolphosphorylcholine, adrenate, 3-methyl-2-oxo-pentanoate, 2-methylsuccinate, 1-octadecanol, 2-aminoadipate, 3-hydroxyisobutyrate, alpha-tocopherol, arginine, betaine, decanoylcarnitine, docosatetraenoic acid, glutamic acid, linoleic acid, linolenic acid, margaric acid, N-acetylglycine, octanoylcarnitine, palmitate, palmitoleic acid, palmitoyl lysophosphatidylcholine, stearate, threonine, and tryptophan.

Embodiment 45

A compound represented by formula (I):

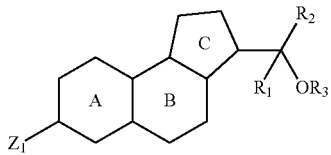

(I)

or a pharmaceutically acceptable salt thereof, wherein:

Rings A, B and C are optionally substituted with one or more substituents selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl (C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl;

Z$_1$ is —OH, —OR$^a$, —OSO$_3$H, —OPO(OH)$_2$, —OC(=O)R$^b$, —OC(=O)NR$^c$R$^d$ or =O;

R$_1$ is a (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$) heterocycloalkyl(C$_2$-C$_6$)alkynyl, aryl, aryl(C$_1$-C$_6$)alkyl, aryl (C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$) alkynyl;

R$_2$ is H, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$) heterocycloalkyl(C$_2$-C$_6$)alkynyl, aryl, aryl(C$_1$-C$_6$)alkyl, aryl (C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$) alkynyl;

R$_3$ is H, —C(=O)R$^b$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$) heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, heteroaryl(C$_2$-C$_6$)alkynyl;

or OR$_3$ together with R$_2$ forms a 3 to 9 membered ring optionally substituted with =O, (C$_1$-C$_6$)alkyl, —OH or —OR$^a$;

R$^a$ is (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$) alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl (C$_2$-C$_6$)alkenyl, aryl(C$_2$-C$_6$)alkynyl, heteroaryl, heteroaryl (C$_1$-C$_6$)alkyl, heteroaryl(C$_2$-C$_6$)alkenyl, heteroaryl(C$_2$-C$_6$) alkynyl;

R$^b$ is H or a (C$_1$-C$_6$)alkyl;

R$^c$ and R$^d$ are each independently H or a (C$_1$-C$_6$)alkyl; and

R$^e$, R$^f$, R$^g$ and R$^h$ are each independently H or a (C$_1$-C$_6$) alkyl;

wherein each of (C$_1$-C$_6$)alkyl, (C$_2$-C$_6$) alkenyl, (C$_2$-C$_6$) alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkenyl, (C$_3$-C$_9$)heterocycloalkyl(C$_2$-C$_6$)alkynyl, aryl, aryl(C$_1$-C$_6$)alkyl, aryl(C$_2$-C$_6$)alkenyl, aryl(C$_2$-C$_6$)alkynyl, heteroaryl, heteroaryl(C$_1$-C$_6$)alkyl, heteroaryl(C$_2$-C$_6$)alkenyl, and heteroaryl(C$_2$-C$_6$)alkynyl groups described above is optionally substituted with 1 to 5 substituents independently selected from the group consisting of halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, halo(C$_1$-C$_6$)alkyl and hydroxyl(C$_1$-C$_6$)alkyl.

Embodiment 46

The compound of Embodiment 45, wherein the compound is represented by structural formula (II):

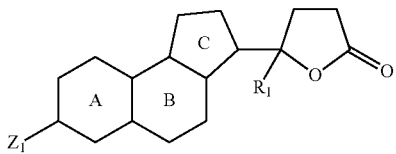

(II)

or a pharmaceutically acceptable salt thereof, wherein Z$_1$ is —OR$^a$, —OSO$_3$H, —OPO(OH)$_2$, —OC(=O)R$^b$, or —OC(=O)NR$^c$R$^d$.

Embodiment 47

The compound of Embodiment 46, wherein the compound is represented by structural formula (III):

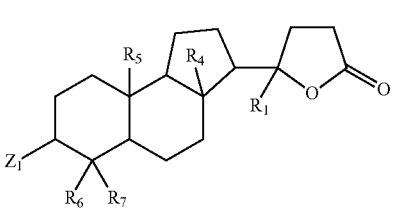

(III)

or a pharmaceutically acceptable salt thereof, wherein:

R$_4$, R$_5$, R$_6$ and R$_7$ are each independently selected from the group consisting of —H, halogen, —CN, —NO$_2$, —OR$^e$, —SR$^e$, —NR$^f$R$^g$, —C(=O)OR$^e$, —OC(=O)R$^e$, —C(=O)R$^e$, —C(=O)NR$^f$R$^g$, —OC(=O)NR$^f$R$^g$, —NR$^h$C(=O)R$^e$, —NR$^h$C(=O)OR$^e$, (C$_1$-C$_6$)alkyl, (C$_2$-C$_6$) alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkenyl, (C$_3$-C$_8$)cycloalkyl(C$_2$-C$_6$)alkynyl, (C$_3$-C$_9$)heterocycloalkyl, (C$_3$-C$_9$)heterocycloalkyl(C$_1$-C$_6$)alkyl, (C$_3$-C$_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl;

wherein each of ($C_1$-$C_6$)alkyl, ($C_2$-$C_6$) alkenyl, ($C_2$-$C_6$) alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkenyl, ($C_3$-$C_8$)cycloalkyl($C_2$-$C_6$)alkynyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkenyl, ($C_3$-$C_9$)heterocycloalkyl($C_2$-$C_6$)alkynyl, aryl, aryl($C_1$-$C_6$)alkyl, aryl($C_2$-$C_6$)alkenyl, aryl($C_2$-$C_6$)alkynyl, heteroaryl, heteroaryl($C_1$-$C_6$)alkyl, heteroaryl($C_2$-$C_6$)alkenyl, and heteroaryl($C_2$-$C_6$)alkynyl groups described above is optionally substituted with 1 to 5 substituents independently selected from the group consisting of halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^h$C(=O)$R^e$, —$NR^h$C(=O)$OR^e$, ($C_1$-$C_6$)alkyl, halo($C_1$-$C_6$)alkyl and hydroxyl($C_1$-$C_6$)alkyl.

Embodiment 48

The compound of any one of Embodiments 45 to 47, wherein $R_1$ is a ($C_1$-$C_6$)alkyl.

Embodiment 49

The compound of Embodiment 48, wherein $R_1$ is methyl.

Embodiment 50

The compound of any one of Embodiments 47 to 49, wherein $R_4$, $R_5$, $R_6$ and $R_7$ are each independently —H, halogen, —CN, —$NO_2$, —$OR^e$, —$SR^e$, —$NR^fR^g$, —C(=O)$OR^e$, —OC(=O)$R^e$, —C(=O)$R^e$, —C(=O)$NR^fR^g$, —OC(=O)$NR^fR^g$, —$NR^h$C(=O)$R^e$, —$NR^h$C(=O)$OR^e$, ($C_1$-$C_6$)alkyl, halo($C_1$-$C_6$)alkyl and ($C_1$-$C_3$)alkoxy($C_1$-$C_6$)alkyl.

Embodiment 51

The compound of Embodiment 50, wherein $R_4$, $R_5$, $R_6$ and $R_7$ are each independently ($C_1$-$C_6$)alkyl or halo($C_1$-$C_6$)alkyl.

Embodiment 52

The compound of Embodiment 51, wherein $R_4$, $R_5$, $R_6$ and $R_7$ are all methyl.

Embodiment 53

The compound of Embodiment 45, wherein the compound is represented by the structural formula (IV):

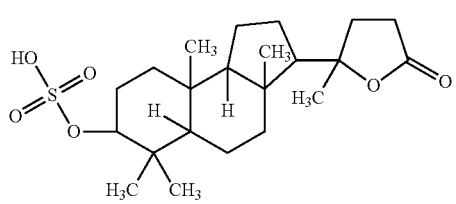

or a pharmaceutically acceptable salt thereof.

Embodiment 54

The compound of Embodiment 45, wherein the compound is:

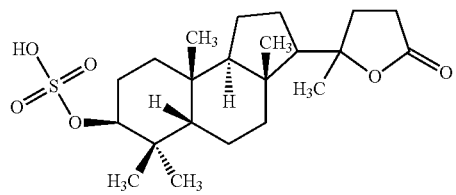

or a pharmaceutically acceptable salt thereof.

Embodiment 55

The compound of Embodiment 54, wherein the compound is at least 60% optically pure.

Embodiment 56

The compound of Embodiment 54, wherein the compound is at least 70% optically pure.

Embodiment 57

The compound of Embodiment 54, wherein the compound is at least 80% optically pure.

Embodiment 58

The compound of Embodiment 54, wherein the compound is at least 90% optically pure.

Embodiment 59

The compound of Embodiment 54, wherein the compound is at least 95% optically pure.

Embodiment 60

The compound of Embodiment 54, wherein the compound is at least 99% optically pure.

Embodiment 61

The compound of any one of Embodiments 45 to 60, wherein the compound is substantially free of impurities.

Embodiment 62

The compound of Embodiment 61, wherein the compound is at least 60% pure.

Embodiment 63

The compound of Embodiment 61, wherein the compound is at least 70% pure.

Embodiment 64

The compound of Embodiment 61, wherein the compound is at least 80% pure.

Embodiment 65

The compound of Embodiment 61, wherein the compound is at least 90% pure.

Embodiment 66

The compound of Embodiment 61, wherein the compound is at least 95% pure.

Embodiment 67

The compound of Embodiment 61, wherein the compound is at least 99% pure.

Embodiment 68

A pharmaceutical composition comprising a pharmaceutically acceptable carrier or diluent and a compound of any one of Embodiments 45 to 67 or a pharmaceutically acceptable salt thereof.

What is claimed is:

1. A method of preparing a compound represented by the following formula:

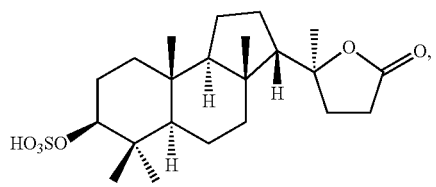
(VII)

or a salt thereof, comprising the steps of:
(1) isolating a compound of formula 3 from *Ailanthus triphysa*

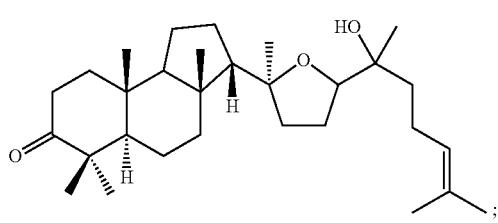
3

(2) reacting the compound of formula 3 with an oxidizing reagent to give a compound of formula 4:

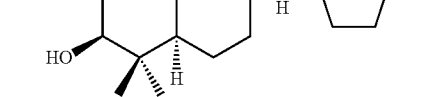
4

(3) reacting the compound of formula 4 with a reducing reagent to give a compound of formula 5:

5

(4) reacting the compound of formula 5 with sulfuric acid to give the compound of formula (VII).

2. The method of claim 1, wherein the compound of formula 3 is isolated by extracting the resins of *Ailanthus triphysa* with an organic solvent.

3. The method of claim 2, wherein the organic solvent is hexane.

4. The method of claim 1, wherein the oxidizing reagent is PCC.

5. The method of claim 1, wherein the reducing reagent is LiAlH$_4$ or NaBH$_4$.

6. The method of claim 1, wherein the compound of formula (VII) is labeled.

* * * * *